(12) United States Patent
De Billot et al.

(10) Patent No.: US 7,687,434 B2
(45) Date of Patent: *Mar. 30, 2010

(54) METHOD OF IMPROVING YIELD AND VIGOR OF PLANTS

(75) Inventors: Maurice R. De Billot, Royston (GB); Schalk Van Wyk, Potchefstroom (ZA); Theunis E. M. Odendaal, Potchefstroom (ZA); Dennis Paul Phillion, St. Charles, MO (US); Jeffrey S. Coultas, Northfield, MN (US); Ernest F. Sanders, St. Louis, MO (US); Greg A. Penner, Winnipeg (CA); Jawed Asrar, Chesterfield, MO (US); Michael K. Stern, Clayton, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/026,301

(22) Filed: Dec. 19, 2001

(65) Prior Publication Data

US 2003/0114308 A1 Jun. 19, 2003

Related U.S. Application Data

(60) Provisional application No. 60/257,502, filed on Dec. 22, 2000.

(51) Int. Cl.
*A01N 25/26* (2006.01)
*A01N 37/00* (2006.01)
(52) U.S. Cl. ..................... 504/100; 504/288
(58) Field of Classification Search ......... 514/405–421, 514/430, 448, 438; 504/128, 100, 288; 424/405–421
See application file for complete search history.

(56) References Cited

U.S. PATENT DOCUMENTS

| | | | | |
|---|---|---|---|---|
| 4,136,486 A * | 1/1979 | Franklin et al. | ......... | 47/58.1 R |
| 5,482,974 A | 1/1996 | Phillion et al. | ......... | 514/619 |
| 5,486,621 A * | 1/1996 | Phillion et al. | ......... | 549/4 |
| 5,498,630 A * | 3/1996 | Phillion et al. | ......... | 514/443 |
| 5,693,667 A * | 12/1997 | Phillion et al. | ......... | 514/461 |
| 5,705,513 A * | 1/1998 | Phillion et al. | ......... | 514/354 |
| 5,739,140 A | 4/1998 | Clinton et al. | ......... | 514/269 |
| 5,811,411 A * | 9/1998 | Phillion et al. | ......... | 514/63 |
| 5,834,447 A * | 11/1998 | Phillion et al. | ......... | 514/63 |
| 5,849,723 A * | 12/1998 | Phillion et al. | ......... | 514/63 |
| 5,914,451 A * | 6/1999 | Martinell et al. | ......... | 800/300 |
| 5,994,270 A * | 11/1999 | Phillion et al. | ......... | 504/193 |
| 5,998,466 A | 12/1999 | Phillion et al. | ......... | 514/443 |
| 6,028,101 A | 2/2000 | Phillion et al. | ......... | 514/469 |
| 6,232,270 B1 * | 5/2001 | Branly et al. | ......... | 504/117 |
| 6,277,847 B1 * | 8/2001 | Theodoridis et al. | ......... | 504/242 |
| 6,559,136 B1 * | 5/2003 | Mauler-Machnik et al. | ... | 514/63 |
| 6,992,047 B2 * | 1/2006 | Asrar et al. | ......... | 504/359 |
| 7,098,170 B2 * | 8/2006 | Asrar et al. | ......... | 504/242 |
| 2003/0060371 A1 * | 3/2003 | Asrar et al. | ......... | 504/272 |
| 2004/0023802 A1 * | 2/2004 | Asrar et al. | ......... | 504/100 |
| 2005/0233905 A1 * | 10/2005 | De Billot et al. | ......... | 504/102 |

FOREIGN PATENT DOCUMENTS

| | | | |
|---|---|---|---|
| EP | 067 479 | * | 12/1982 |
| EP | 0538231 A1 | | 10/1992 |
| WO | WO 93/07751 | | 4/1993 |
| WO | WO 96/18631 | | 6/1996 |

OTHER PUBLICATIONS

J.B. Sinclair, Fungicide Sprays for the Control of Seedborne Pathogens of Rice, Soybeans and Wheat, 1981, Seed Science and Technology, vol. 9, pp. 697-705.*
Roy et al, Isolation of *Gaeumannomyces graminis* var. *graminis* from Soybeans in the Midwest, Plant Disease, vol. 66, No. 9, pp. 822-825.*
Beale et al, MON65500: A Unique Fungicide for the Control of Take-All in Wheat, 1998, The 1998 Brighton Conference—Pests and Diseases, pp. 343-350.*
Von G. Mindt, MON65500- das neue Fungizid gegen die Schwarzbeinigkeit, 1999, Gesunde Pflanzen, Pflanzenschutz, verbraucherschutz, umweltschutz, 103-104, 106, 108-110, 112, 117, 134-148, 150, and 153-158o. 51, No. 7, pp. 240-247.*
Anderson, J.M., et al, "Items for the United States—Indiana," Annual Wheat Newsletter, vol. 46, U.S.A., downloaded from website address wheat.pw.usda.gov. on Nov. 9, 2000.
"Rival & Allegiance-FL," AGRIPROTREAT, downloaded from website address www.agripro.com/seeds/Treatments on Nov. 9, 2000.
"Crop Profile for Soybeans in Illinois," USDA OPMP & PIAP, Feb. 2000, downloaded from website address pestdata.ncsu.edu/crop-profiles on Nov. 4, 2000.
"Monsanto launches wheat disease remedy in Ireland," Irish Biotech News, Oct. 1999, No. 55, downloaded from website address www.biores-irl.ie on Nov. 9, 2000.
Wiesbrook, Michelle, "Agronomic," Illinois Pesticide Review, vol. 1999, issue 5, Sep. 1999, U.S.A., downloaded from website address www.aces.uiuc.edu on Nov. 9, 2000.
"Crop Profile for Soybeans in Iowa," USDA OPMP & PIAP, Feb. 1999, downloaded from website address pestdata.ncsu.edu/crop-profiles on Nov. 4, 2000.
"A Guide to Take-All, A Disease in Cereal Grains," Monsanto Food Health Hope™, 1998, downloaded from website address www.takeall.com on Nov. 4, 2000.
Int'l. Search report for Serial No. PCT/US01/50484 dated Jun. 7, 2002.

(Continued)

*Primary Examiner*—Alton N Pryor
(74) *Attorney, Agent, or Firm*—Nelson Mullins Riley & Scarborough LLP

(57) ABSTRACT

A method of improving the yield and vigor of agronomic plants, in particular leguminous plants such as soybeans, involves treating such plants and/or the propagation material of plants with a composition that includes an active agent, such as a fungicide, that has no significant activity against fungal plant pathogens of the treated plant. When the plant is not wheat, a preferred agent of this type is 4,5-dimethyl-N-(2-propenyl)-2-(trimethylsilyl)-3-thiophenecarboxamide (silthiofam). Plants and plant propagation material, such as seeds, that have been treated by the novel method are also described.

16 Claims, 7 Drawing Sheets

OTHER PUBLICATIONS

Abstract XP-0022200012, Joseph-Horne et al., Silthiofam Interferes with Mitochondrial Function in Take-All Disease of Wheat (2000).

Abstract XP-002200013, Joseph-Home et al., Identification and Characterization of the Mode of Action of Mon 65500: A Novel Inhibitor of ATP Export from Mitochondria of the Wheat Take-All Fungus, *Gaeumannomyces graminis* var. *tritici* (2000).

Abstract XP-002200014, Spink et al., The Effects of a Novel Seed Treatment, Mon 65500, on Take-All Severity and Crop Growth in Winter Wheat (1998).

Revellin, C., Effects of Some Fungicide Seed Treatments on the Survival of *Bradyrhizobium japonicum* and on the Nodulation and Yield of Soybean, 1993, Springer-Verlag, Biology and Fertility of Soils, 16, 211-214.

* cited by examiner

METHOD OF IMPROVING YIELD AND VIGOR OF PLANTS

The present application claims the benefit of U.S. Provisional Application Ser. No. 60/257,502 filed Dec. 22, 2000, which is incorporated herein by reference thereto.

BACKGROUND OF THE INVENTION (1) Field of the Invention

The present invention relates to the improvement of the yield and vigor of agronomic plants, and more particularly to a method of improving the yield and vigor of agronomic plants by treatment of the plant or its propagation material with certain active agents.

(2) Description of the Related Art

Plants, and in particular, legumes, are a critical source of food, animal feed, fiber, and useful chemicals and medicaments. The ability of legumes to fix nitrogen provides this order of plants with the unusual ability to provide high quality nutritional proteins as well as to improve the nitrogen content of the soils in which they grow. One species of legume—the soybean—is an ancient and important worldwide crop. Relatively easy to grow and subject to relatively few important insect pests, compared with other important agronomic crops, soybeans provide oil and high protein meal for human and animal consumption and for industrial uses.

In the United States, about 70 million acres are planted to soybeans each year and recent annual soybean production has been over 2.5 billion bushels. The average yield of soybeans in the United States has been steadily increasing over the past 75 years from an initial level of about 11 bu/ac, to the present level of about 35 to 40 bu/ac. (See, *United States Department of Agriculture, National Agricultural Statistics Service, Crop Report*, June 2000, Washington, D.C.). Better strains of seed and the systematic improvement of agricultural and pest management practices have facilitated this improvement.

Where the growing season permits in the Midwestern United States, soybeans are typically grown in rotation with field corn and sometimes in a double-crop after winter wheat is harvested. Conservation tillage practices are regularly used for soybeans and from one-fourth to about one-third of the acreage is no-tilled. About two-thirds of all soybeans are solid seeded (sown in narrow, 6", 7", or 8" rows). The benefits of solid seeding a soybean crop are that the canopy closes quickly and can reduce weed growth and, hence the need for late season post emergence herbicides. This eliminates the possibility of row cultivation and late season application of pesticides by ground application.

In the U.S. Midwest, soybeans are rarely treated for insect pests, and the few insects that can cause crop loss include bean leaf beetle (*Ceriotoma trifurcata*), grasshoppers (*Melanoplus* spp.), green cloverworm (*Plathypena scabra*), and potato leafhopper (*Empoasca fabae*).

Soybean yield can be adversely affected by several diseases, and among these are pythium damping off (*Pythium* spp.), phytophthera damping off (*Phytophthera* spp.), rhizoctonia root rot (*Rhizoctonia solani*), anthracnose (*Colletotrichum* spp.), stem canker (*Diaporthe phaseolorum*), septoria leaf spot (*Septoria glycines*), purple seed stain (*Cercospora kikuchii*), sudden death syndrome (*Fusarium solani*), white mold (*Sclerotinia sclerotinorum*), and brown stem rot (*Phialophora gregata*). It is known, however, that non-pesticidal management measures are equal to or better than pesticides for the control of many common pathogens. Plant disease management for soybeans has always relied more on agronomic practices than on pesticides, and seed treatment and foliar fungicides, along with nematicides, play a limited role. (See, e.g., information dealing with soybeans on U.S. Department of Agriculture website: http://pestdata.ncsu.edu/crop-profiles/, dated Nov. 4, 2000).

Diseases such as "Take-all disease", caused by the organism *Gaerumannomyces graminis*, which are prevalent in cereal crops, have not been reported to affect soybeans.

Seed treatment with fungicides, such as metalaxyl, carboxin, captan and thiram, which are active against the known soybean disease-causing organisms listed above, is common for soybeans, and the impact of fungicidal seed treatment on yield due to the avoidance of stand losses due to these diseases is significant. However, the cost of such seed treatment is modest relative to overall production costs. Moreover, since several fungicides are approved for use on soybeans, if one or two of the fungicides were to be withdrawn, it is likely that one or more other known compounds would be adequate substitutes. Therefore, the incentive to search for different fungicides to act as fungicidal seed treatment compounds for soybeans has been slight.

However, with the limited amount of high quality arable land that is available for row crop production in regions having suitable climate, any method that would improve the vigor and yield of agronomic plants in general, and in particular, for legumes, such as soybeans, would provide a significant advantage. It would be particularly useful if such method was easy to.

SUMMARY OF THE INVENTION

Briefly therefore, the present invention is directed to a novel method of increasing the vigor and/or the yield of an agronomic plant comprising treating the plant or its propagation material with a composition which comprises an effective amount of a fungicide which has no significant activity against fungal plant pathogens for such agronomic plant.

The present invention is also directed to a novel method of increasing the vigor and/or the yield of an agronomic plant except for wheat comprising treating an agronomic plant or its propagation material except for wheat with a composition comprising an effective amount of an active agent that has activity against *Gaerumannomyces graminis*.

The present invention is also directed to a novel agronomic plant or its propagation material for which *Gaerumannomyces graminis* is not a disease-causing organism, wherein the plant or its propagation material has been treated with a composition comprising an effective amount of an active agent which has activity against *Gaerumannomyces graminis*, and wherein the plant is not wheat.

The present invention is also directed to a novel plant or its propagation material which has been treated with a composition comprising a fungicide in an amount sufficient to increase the yield and/or the vigor of the plant, wherein the fungicide is one having no significant activity against fungal plant pathogens of said plant or its propagation material.

The present invention is also directed to a novel plant or its propagation material of the family Fabaceae which has been treated with a composition comprising an active agent which has activity against *Gaerumannomyces graminis* in an amount sufficient to increase the yield and/or the vigor of said plant.

The present invention is also directed to a novel seed that has been treated by the method described first above.

The present invention is also directed to a novel method for increasing the vigor and/or the yield of an agronomic plant or its propagation material comprising treating the seed and/or the foliage of such plant with a compound having the formula:

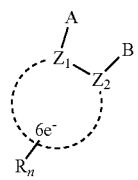

wherein $Z_1$ and $Z_2$ are C or N and are part of an aromatic ring selected from benzene, pyridine, thiophene, furan, pyrrole, pyrazole, thiazole, and isothiazole;

A is selected from —C(X)-amine, —C(O)—SR$_3$, —NH—C(X)R$_4$, and —C(=NR$_3$)—XR$_7$;

B is —W$_m$—Q(R$_2$)$_3$ or selected from o-tolyl, 1-naphthyl, 2-naphthyl, and 9-phenanthryl, each optionally substituted with halogen or R$_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) C$_1$-C$_4$ alkyl, alkenyl, alkynyl, C$_3$-C$_6$ cycloalkyl, and cycloalkenyl, each optionally substituted with halo, hydroxy, thio, amino, nitro, cyano, formyl, phenyl, C$_1$-C$_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, C$_1$-C$_4$ alkyl, alkenyl, alkynyl, alkoxy, alkylthio, alkylamino, dialkylamino, haloalkyl, and haloalkenyl;

d) C$_1$-C$_4$ alkoxy, alkenoxy, alkynoxy, C$_3$-C$_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring; each R$_2$ is independently selected from alkyl, alkenyl, alkynyl, cycloalkyl, cycloalkenyl and phenyl, each optionally substituted with R$_4$ or halogen; and wherein, when Q is C, R$_2$ may also be selected from halo, alkoxy, alkylthio, alkylamino, and dialkylamino;

wherein two R$_2$ groups may be combined to form a cyclo group with Q;

R$_3$ is C$_1$-C$_4$ alkyl;

R$_4$ is C$_1$-C$_4$ alkyl, haloalkyl, alkoxy, alkylthio, alkylamino, or dialkylamino;

R$_7$ is C$_1$-C$_4$ alkyl, haloalkyl, or phenyl, optionally substituted with halo, nitro, or R$_4$;

or an agronomic salt thereof, except that the agronomic plant is not wheat when the compound is silthiofam.

The present invention is also directed to a novel method for increasing the vigor and/or the yield of an agronomic plant or its propagation material comprising treating the seed and/or the foliage of such plant with a compound having the formula:

(a)
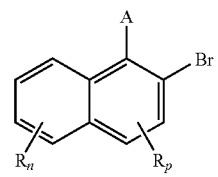

(b)
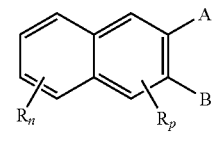

(c)
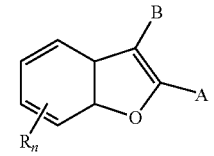

(d)
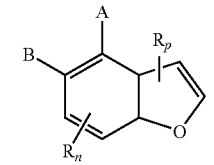

(e)
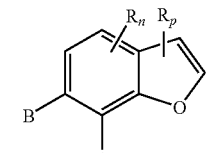

(f)
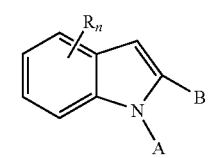

(g)

(h)
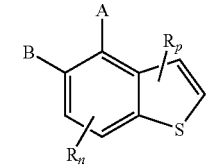

(i)
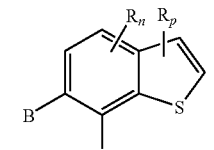

-continued

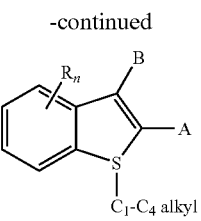

(j)

where A is —C(X)-amine; B is —W$_m$—Q(R$_2$)$_3$; and A can be B when B is A except when the formula is f), then Q cannot be Si;

Q is C or Si;

W is —NH—, —O— or NCH$_3$—;

X is O or S;

m is 0 or 1, provided that m is 0 when Q is Si;

n is 0, 1, 2, or 3;

p is 0, 1 or 2, and n plus p is equal to or less than 3;

each R is independently selected from a) halo, formyl, cyano, amino, nitro, thiocyanato, isothiocyanato, trimethylsilyl, and hydroxy;

b) C$_1$-C$_4$ alkyl, alkenyl, alkynyl, C$_3$-C$_6$ cycloalkyl, and cycloalkenyl, each optionally substituted with halo, hydroxy, thio, amino, nitro, cyano, formyl, phenyl, C$_1$-C$_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, C$_1$-C$_4$ alkyl, alkenyl, alkynyl, alkoxy, alkylthio, alkylamino, dialkylamino, haloalkyl, and haloalkenyl;

d) C$_1$-C$_4$ alkoxy, alkenoxy, alkynoxy, C$_3$-C$_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo; each R$_2$ is independently selected from alkyl, alkenyl, alkynyl, cycloalkyl, cycloalkenyl and phenyl, each optionally substituted with R$_4$ or halogen; and wherein, when Q is C, R$_2$ may also be selected from halo, alkoxy, alkylthio, alkylamino, and dialkylamino; wherein two R$_2$ groups may be combined to form a cyclo group with Q; R$_4$ is C$_1$-C$_4$ alkyl, haloalkyl, alkoxy, alkylthio, alkylamino, or dialkylamino;

or an agronomic salt thereof.

The present invention is also directed to a novel method for increasing the vigor and/or the yield of an agronomic plant or its propagation material comprising treating the seed and/or the foliage of such plant with a compound having the formula:

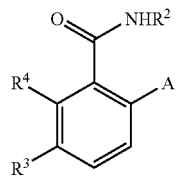

wherein R$^2$ is ethyl, iso-propyl, propyl or allyl;

A is N(CH$_3$)$_{1-n}$H$_n$R$^5$ or OR$^6$ wherein n is 0 or 1, R$^5$ is (CH$_3$)$_m$(CH$_3$CH$_2$)$_{3-m}$C, 1-methyl-1-cyclopentyl, 1-methyl-1-cyclohexyl or 2,3-dimethyl-2-butyl wherein m is 0, 1, 2 or 3 and R$^6$ is independently R$^5$, or 2,3,3-trimethyl-2-butyl;

R$^3$ is H or independently R$^4$; and

R$^4$ is halo or CH$_3$;

with the proviso that when A is N(CH$_3$)$_{1-n}$H$_n$R$^5$, if R$^3$ is H and R$^5$ is 1-methyl-1-cyclohexyl or (CH$_3$)$_m$(CH$_2$CH$_3$)$_{3-m}$C, where m is 0 or 3, or if R$^3$ is halo and R$^2$ is (CH$_3$)$_m$(CH$_3$CH$_2$)$_{3-m}$C, where m is 3, then R$^2$ cannot be ethyl;

and with the proviso that when A is OR$^6$ then m is equal to or less than 2, and if R$^3$ is H or halo and R$^2$ is ethyl or isopropyl, then R$^6$ is (CH$_3$)$_M$(CH$_3$CH$_2$)$_{3-M}$C where m is 1;

or an agronomic salt thereof.

The present invention is also directed to a novel method for increasing the vigor and/or the yield of an agronomic plant or its propagation material except for wheat comprising treating the seed and/or the foliage of such plant with silthiofam.

Among the several advantages found to be achieved by the present invention, therefore, may be noted the provision of a method that improves the vigor and yield of agronomic plants in general, and in particular, for legumes, such as soybeans, the provision of a such a method that is easy to apply.

DETAILED DESCRIPTION OF THE PREFERRED EMBODIMENTS

Figure 1:
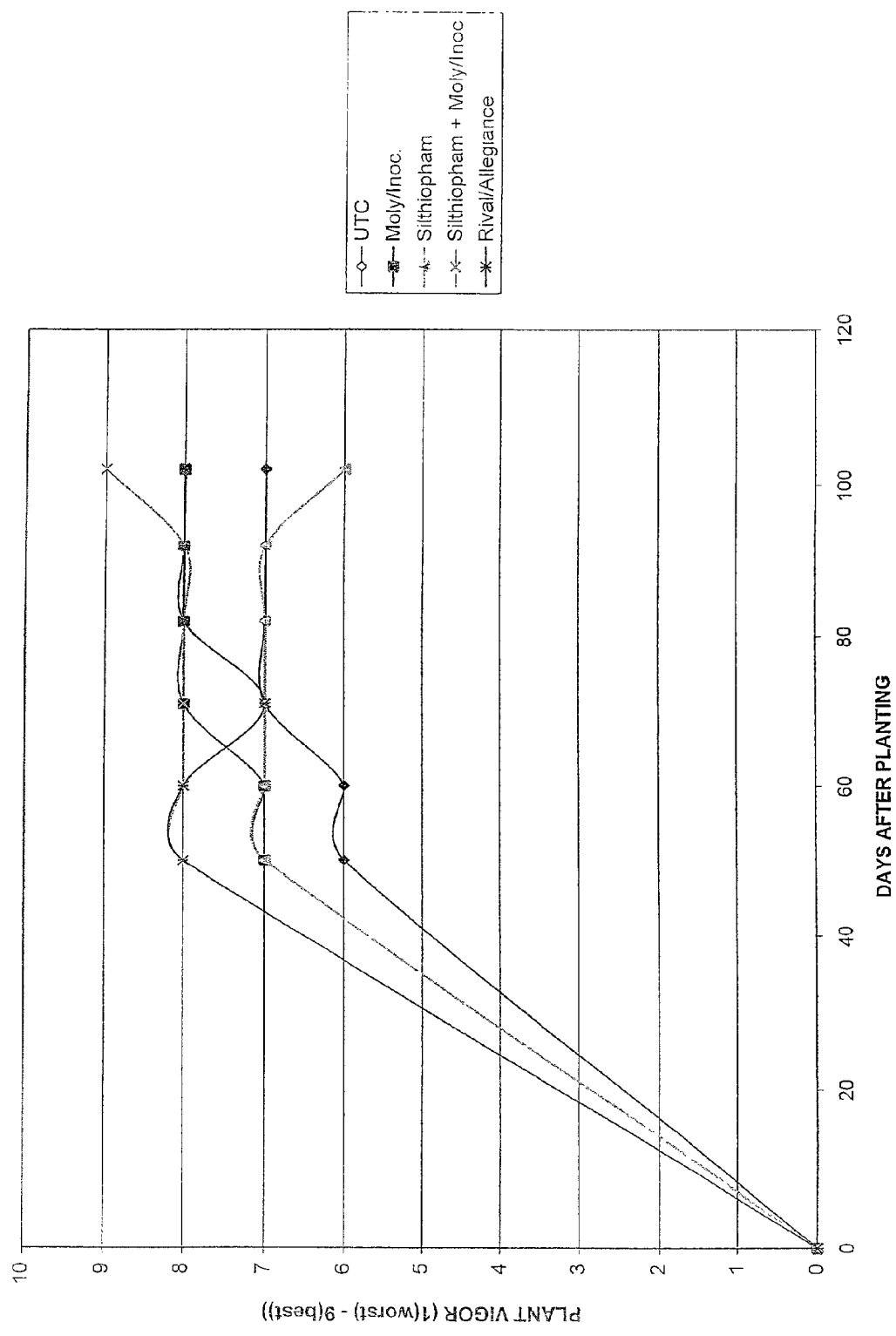
FIG. 1 is a plot of vigor of soybean plants in a field trial as a function of time after planting for soybeans receiving no treatment prior to planting compared with soybeans that had been treated prior to planting with silthiopham, silthiopham+inoculant, a sticker+inoculant, and a standard fungicide treatment.

In accordance with the present invention, it has been discovered that the vigor and/or the yield of an agronomic plant can be increased by treating the seed and/or the foliage of the plant with a composition that contains an effective amount of an active agent, in particular a fungicide, which has no significant activity against fungal plant pathogens of the treated plant. However, the active agent can have activity against plant pathogens which are not known to cause disease in the plant that has received the treatment. The increase in yield and/or vigor is entirely unexpected because it is counterintuitive to apply an agent to a plant where the agent is not known to be active against pathogens that cause disease in that plant. In fact, given the care expended upon minimizing the use of resources in modern farming practices, such an application would be considered to be a waste. But, surprisingly, the inventors have found that this is not the case.

When the plant is other than wheat, and in particular when the plant is of the family Fabaceae, treatment of the seed and/or the foliage of the plant with certain active agents that are known to have activity against the fungus *Gaerumannomyces graminis* (Gg), and, in particular against the Gg variety *tritici*, results in a surprising improvement in the yield and vigor of such plants. As discussed above, this improvement is unexpected because the improvement has been shown even in plants for which *Gaerumannomyces graminis* var. *tritici* is not a known disease-causing agent. In fact, the increase in yield and vigor is seen to occur even when the active agent does not demonstrate significant activity against organisms that are commonly known to cause disease in the treated plant. Nonetheless, when these active agents have been applied to soybeans, for example, the crop has shown very significant improvements in both yield and vigor—and yield increases up to about 20% over non-treated controls have been reported. This effect was unexpected because the organism *Gaerumannomyces graminis* var. *tritici* is not known to have any detrimental effect on soybeans, and the active agent that was used to treat the soybeans was shown to have little activity against the commonly known disease-causing organisms for that crop.

Since the active agents that are useful in the novel method can be applied to plant propagation material such as seed prior to planting, the present method provides an easy method of achieving the advantages of improved plant yield without the added effort and expense of cultivation or in-field application after germination and sprouting.

Alternatively, the subject method can be applied to plants after they have sprouted, such as by foliar application by spraying or dusting. When this embodiment is used, the active agent can also be combined, if desired, with other herbicides or pesticides to obtain further beneficial results. When the active agent is used with herbicides, it is preferred that the plant be a transgenic plant having a transgenic event that provides resistance to the particular herbicide being used.

When the terms "plant propagation material" is used herein, it is meant to include plant seeds, cuttings, sets, rhizomes, tubers, meristem tissue, single and multiple plant cells, and any other plant tissue from which a complete plant can be obtained.

When it is said that an active agent is known to "have activity against *Gaerumannomyces graminis*", it is meant that the agent has some degree of biostatic or biocidal activity against that organism when it is contacted with the organism under conditions that are conventionally employed for the determination of an $EC_{50}$ value for the agent upon that organism. As used herein, the term "$EC_{50}$" means the median effective concentration of an active agent against a particular organism. The method for determining the $EC_{50}$ value for a fungicide is described by Nuninger-Ney et al., In vitro test method for assessment of propiconazole sensitivity in *Pyrenophora teres* isolates, FRAC Methods for Monitoring Fungicide Resistance, EPPO Bulletin, 21:291-354 (1991). It is preferred that the active agent is one that has an $EC_{50}$ value against *Gaerumannomyces graminis* var. *tritici* of not over about 10 µg/ml, more preferred that the $EC_{50}$ value be not over about 1 µg/ml, even more preferred that the $EC_{50}$ value be not over about 0.1 µg/ml, and yet more preferred that the $EC_{50}$ value be not over about 0.01 µg/ml against *Gaerumannomyces graminis* var. *tritici*.

The active agent of one embodiment of the subject method can be one that not only has activity against *Gaerumannomyces graminis*, but also can have no significant activity against the diseases that are commonly known to attack the plant to be treated with the subject method. By way of example, a preferred active agent for use on soybeans is one having activity against *Gaerumannomyces graminis* var. *tritici*, but having no significant activity against such diseases as phytophthera damping off (*Phytophthera* spp.), rhizoctonia root rot (*Rhizoctonia solani*), anthracnose (*Colletotrichum* spp.), septoria leaf spot (*Septoria glycines*), and sudden death syndrome (*Fusarium solani*), which are diseases that are known to attack soybeans.

When a "fungal plant pathogen" is referred to, what is meant is a fungal strain known to be an important pathogen of a particular plant. For example, *Gaerumannomyces graminis* is a known plant pathogen for wheat.

When it is said that an active agent has only "weak, or no activity", or "no significant activity", against a certain disease-causing organism, what is meant is that the active agent is not sufficient to control the particular organism when used in agronomically reasonable levels. It is preferred that an active agent having no significant activity against a disease-causing organism has an $EC_{50}$ value against such organism of over about 10 µg/ml, preferably greater than about 20 µg/ml.

As used herein, the terms "agronomic plant" and "agronomically important plant" mean the same thing, and both refer to a plant of which a part or all is, or has been, harvested or cultivated on a commercial scale, or serves as an important source of feed, food, fiber or other chemical compounds. Without limitation, some examples of such plants are corn, cereals, including wheat, barley, rye, and rice, vegetables, clovers, legumes, including beans, peas and alfalfa, sugar cane, sugar beets, tobacco, cotton, rapeseed (canola), sunflower, safflower, and sorghum. In an embodiment of the invention where the active agent is one that has activity against *Gaerumannomyces graminis*, wheat is not considered to be an agronomic plant for the purposes of this specification.

When the subject method is described herein as "increasing the yield" of an agronomic plant, what is meant is that the yield of a product of the plant is increased by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. By way of example, if untreated soybeans yielded 35 bu/ac, and if soybeans that received the subject treatment yielded 38 bu/ac under the same growing conditions, then the yield of soybeans would be said to have been increased by $(38-35/35) \times 100 = 8.5\%$.

When the subject method is described herein as "increasing the vigor" of an agronomic plant, what is meant is that the vigor rating, or the plant weight, or the plant height, or the plant canopy, or the visual appearance, or any combination of these factors, is increased or improved by a measurable or noticeable amount over the same factor of the plant produced under the same conditions, but without the application of the subject method. It is preferred that such factor(s) is increased or improved by a significant amount.

It is preferred that the method be used with legumes (members of the class Magnoliopsida and the order Fabales). It is more preferred that the plant be in the family Fabaceae (formerly Leguminosae) and the sub-family Papilionoideae or Faboideae, and even more preferred that the plant be selected from the group consisting of *Pisum* spp. (including the garden pea, *P. sativum*), *Medicago* spp. (including alfalfa, *M. sativa*), *Arachis* spp. (including peanuts, *A. hypogaea*), soybeans (including *Glycine max*, *Glycine hispida*), *Vicia* spp. (including vetches), *Vigna* spp. (including cowpeans), *Vicia* spp. (including fava bean, *V. faba*), trefoil, clovers and *Phaseolus* spp. (including *P. vulgaris, P. lunatus, P. limensis,* and *P. coccineus*). It is most preferred that the present invention be used with soybeans.

It is believed that plants and plant propagation material that are suitable for use in the present invention can be non-transgenic plants, or can be plants that have at least one transgenic event. In an embodiment where the subject method includes treatment of the seed and/or the foliage of a plant with a herbicide or other pesticides, it is preferred that the plant be a transgenic plant having a transgenic event that confers resistance to the particular herbicide or other pesticide that is employed. When a herbicide such as glyphosate is included in the treatment, it is preferred that the transgenic plant or plant propagation material be one having a transgenic event that provides glyphosate resistance. Some examples of such preferred transgenic plants having transgenic events that confer glyphosate resistance are described in U.S. Pat. Nos. 5,914,451, 5,866,775, 5,804,425, 5,776,760, 5,633,435, 5,627,061, 5,463,175, 5,312,910, 5,310,667, 5,188,642, 5,145,783, 4,971,908 and 4,940,835. When the transgenic plant is a transgenic soybean plant, such plants having the characteristics of "Roundup-Ready" transgenic soybeans (available from Monsanto Company, St. Louis, Mo.) are preferred.

It is to be understood, however, that when the plant is a transgenic plant, the transgenic events that are present in the plant are by no means limited to those that provide herbicide or pesticide resistance, but can include any transgenic event. In fact, the use of "stacked" transgenic events in a plant is also contemplated.

The present invention is also useful for application to plants and propagation material which have been improved by a program of selective breeding based on quantitative trait loci (QTL) information. Further information about the use of such breeding programs can be found in U.S. Pat. No. 5,476,524, and in Edwards, M. D. et al., *Genetics*, 116:113-125 (1987); Edwards, M. D. et al., *Theor. Appl. Genet.*, 83:765-774 (1992); Paterson, A. H. et al., *Nature*, 335:721-726 (1988); and Lander, E. S. et al., *Mapping Medelian Factors Underlying Quantitative Traits Using RFLP Linkage Maps*, Genetics Society of America, pp. 185-199 (1989).

The present method is particularly useful for application to soybeans for which the yield has been improved through a QTL-directed selective breeding program.

The present method can be applied to any form of the plant that is to be treated, or any propagation material for the plant. For example, the method can be used to treat a plant seed at any time after its formation, or to treat the roots, leaves stems, shoots and/or fruit of the plant at any time after germination.

The active agents that are suitable for use in the present invention include certain chemical compounds that have demonstrated activity against plant pathogenic fungi, and in one embodiment, against *Gaerumannomyces graminis* microorganisms. Such active agents include fungicides that are described in U.S. Pat. Nos. 5,482,974, 5,486,621, 5,498,630, 5,693,667, 5,693,667, 5,705,513, 5,811,411, 5,834,447, 5,849,723, 5,994,270, 5,998,466, 6,028,101, and in publications WO 93/07751, and EP 0 538 231 A1. In particular, such compounds are described in WO 93/07751 and in European Patent Application No. 0 538 231 A1, which describe compounds having the general formula (I), below:

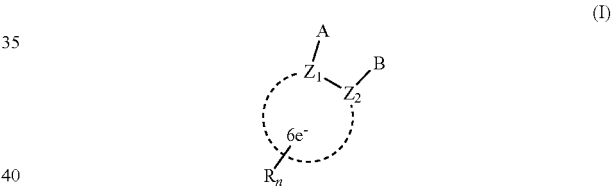

(I)

wherein $Z_1$ and $Z_2$ are C or N and are part of an aromatic ring selected from benzene, pyridine, thiophene, furan, pyrrole, pyrazole, thiazole, and isothiazole;

A is selected from —C(X)-amine, —C(O)—SR$_3$, —NH—C(X)R$_4$, and —C(=NR$_3$)—XR$_7$;

B is —W$_m$—Q(R$_2$)$_3$ or selected from o-tolyl, 1-naphthyl, 2-naphthyl, and 9-phenanthryl, each optionally substituted with halogen or R$_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$-$C_4$ alkyl, alkenyl, alkynyl, $C_3$-$C_6$ cycloalkyl, and cycloalkenyl, each optionally substituted with halo, hydroxy, thio, amino, nitro, cyano, formyl, phenyl, $C_1$-$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$-$C_4$ alkyl, alkenyl, alkynyl, alkoxy, alkylthio, alkylamino, dialkylamino, haloalkyl, and haloalkenyl;

d) $C_1$-$C_4$ alkoxy, alkenoxy, alkynoxy, $C_3$-$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with $R_3$ is $C_1$-$C_4$ alkyl;

$R_4$ is $C_1$-$C_4$ alkyl, haloalkyl, alkoxy, alkylthio, alkylamino, or dialkylamino;

$R_7$ is $C_1$-$C_4$ alkyl, haloalkyl, or phenyl, optionally substituted with halo, nitro, or $R_4$;

or an agronomic salt thereof.

The term "amine" in —C(X)-amine means an unsubstituted, monosubstituted, or disubstituted amino radical, including nitrogen-bearing heterocycles. Examples of substituents for the amino radical include, but are not limited to, hydroxy; alkyl, alkenyl, and alkynyl, which may be straight or branched chain or cyclic; alkoxyalkyl; haloalkyl; hydroxyalkyl; alkylthio; alkylthioalkyl; alkylcarbonyl; alkoxycarbonyl; aminocarbonyl; alkylaminocarbonyl; cyanoalkyl; mono- or dialkylamino; phenyl, phenylalkyl or phenylalkenyl, each optionally substituted with one or more $C_1$-$C_6$ alkyl, alkoxy, haloalkyl, $C_3$-$C_6$ cycloalkyl, halo, or nitro groups; $C_1$-$C_4$ alkyl or alkenyl groups substituted with heterocycles, optionally substituted with one or more $C_1$-$C_4$ alkyl, alkoxy, haloalkyl, halo, or nitro groups. Examples of such nitrogen-bearing heterocycles, which are bonded at a nitrogen to —C(X)—, include, but are not limited to, morpholine, piperazine, piperidine, pyrrole, pyrrolidine, imidazole, and triazoles, each of which may be optionally substituted with one or more $C_1$-$C_6$ alkyl groups.

Specific examples of the amino radicals useful in the present invention include, but are not limited to, ethylamino, methylamino, propylamino, 2-methylethylamino, 1-propenylamino, 2-propenylamino, 2-methyl-2-propenylamino, 2-propynylamino, butylamino, 1,1-dimethyl-2-propynylamino, diethylamino, dimethylamino, N-(methyl)ethylamino, N-(methyl)-1,1(dimethyl)ethylamino, dipropylamino, octylamino, N-(ethyl)-1-methylethylamino, 2-hydroxyethylamino, 1-methylpropylamino, chloromethylamino, 2-chloroethylamino, 2-bromoethylamino, 3-chloropropylamino, 2,2,2-trifluoroethylamino, cyanomethyl, methylthiomethylamino, (methylsulfonyl)oxyethylamino, 2-ethoxyethylamino, 2-methoxyethylamino, N-(ethyl)-2-ethoxyethylamino, 1-methoxy-2,2-dimethylpropylamino, cyclopropylamino, cyclobutylamino, cyclopentylamino, cyclohexylamino, methoxymethylamino, N-(methoxymethyl)ethylamino, N-(1-methylethyl)propylamino, 1-methylheptylamino, N-(ethyl)-1-methylheptylamino, 6, 6-dimethyl-2-hepten-4-ynylamino, 1,1-dimethyl-2-propynylamino. Further examples include benzylamino, ethylbenzylamino, 3-methoxybenzylamino, 3-(trifluoromethyl)benzylamino, N-methyl-3-(trifluoromethyl)benzylamino, 3,4,5-trimethoxybenzylamino, 1,3-benzodioxol-5-ylmethylamino, phenylamino, 3-(1-methylethyl)phenylamino, ethoxyphenylamino, cyclopentylphenylamino, methoxyphenylamino, nitrophenylamino, 1-phenylethylamino, N-(methyl)-3-phenyl-2-propenylamino, benzotriazolylphenylmethyl, 2-pyridinylmethylamino, N-(ethyl)-2-pyridinylmethylamino, 2-thienylmethylamino, and furylmethylamino. Further examples of amino radicals include methylhydrazino, dimethylhydrazino, N-ethylanilino, and 2-methylanilino. The amine may also be substituted with diethyl N-ethylphosphoramidic acid, t-butoxycarbonyl, methoxycarbonyl, ethoxycarbonyl, propoxycarbonyl, etc. Of these examples of the amino radical, ethylamino is preferred.

Examples of B include, but are not limited to, trimethylsilyl, ethyldimethylsilyl, diethylmethylsilyl, triethylsilyl, dimethylpropylsilyl, dipropylmethylsilyl, dimethyl-1-(methyl)ethylsilyl, tripropylsilyl, butyldimethylsilyl, pentyldimethylsilyl, hexyldimethylsilyl, cyclopropyldimethylsilyl, cyclobutyldimethylsilyl, cyclopentyldimethylsilyl, cyclohexyldimethylsilyl, dimethylethenylsilyl, dimethylpropenylsilyl, chloromethyldimethylsilyl, 2-chloroethyldimethylsilyl, bromomethyldimethylsilyl, bicycloheptyldimethylsilyl, dimethylphenylsilyl, dimethyl-2-(methyl)phenylsilyl, dimethyl-2-fluorophenylsilyl, and other such silyl groups of the formula $Si(R_2)_3$; any such silyl group connected to the $Z_1$-$Z_2$ ring by a methylene group; and any of these groups wherein germanium or tin is substituted for silicon. Of these examples of B, trimethylsilyl is preferred.

Further examples of B include 1,1-dimethylethyl, 1,1-dimethylpropyl, 1,1-dimethylbutyl, 1,1-dimethylpentyl, 1-ethyl-1-methylbutyl, 2,2-dimethylpropyl, 2,2-dimethylbutyl, 1-methyl-1-ethylpropyl, 1,1-diethylpropyl, 1,1,2-trimethylpropyl, 1,1,2-trimethylbutyl, 1,1,2,2-tetramethylpropyl, 1,1-dimethyl-2-propenyl, 1,1,2-trimethyl-2-propenyl, 1,1-dimethyl-2-butenyl, 1,1-dimethyl-2-propynyl, 1,1-dimethyl-2-butynyl, 1-cyclopropyl-1-methylethyl, 1-cyclobutyl-1-methylethyl, 1-cyclopentyl-1-methylethyl, 1-(1-cyclopentenyl)-1-methylethyl, 1-cyclohexyl-1-methylethyl, 1-(1-cyclohexenyl)-1-methylethyl, 1-methyl-1-phenylethyl, 1,1-dimethyl-2-chloroethyl, 1,1-dimethyl-3-chloropropyl, 1,1-dimethyl-2-methoxyethyl, 1,1-dimethyl-2-(methylamino)ethyl, 1,1-dimethyl-2-(dimethylamino)ethyl, 1,1-dimethyl-3-chloro-2-propenyl, 1-methyl-1-methoxyethyl, 1-methyl-1-(methylthio)ethyl, 1-methyl-1-(methylamino)ethyl, 1-methyl-1-(dimethylamino)ethyl, 1-chloro-1-methylethyl, 1-bromo-1-methylethyl, and 1-iodo-1-methylethyl. Of these examples of B, 1,1-dimethylethyl is preferred.

Further examples of B are 1,1-dimethylamino, 1,1-dimethylpropylamino, 1,1-dimethylbutylamino, 1,1-dimethylpentylamino, 1-ethyl-1-methylbutylamino, 2,2-dimethylpropylamino, 2,2-dimethylbutylamino, 1-methyl-1-ethylpropylamino, 1,1-diethylpropylamino, 1,1,2-trimethylpropylamino, 1,1,2-trimethylbutylamino, 1,1,2,2-tetramethylpropylamino, 1,1-dimethyl-2-propenylamino, 1,1,2-trimethyl-2-propenylamino, 1,1-dimethyl-2-butenylamino, 1,1-dimethyl-2-propynylamino, 1,1-dimethyl-2-butynylamino, 1-cyclopropyl-1-methylethylamino, 1-cyclobutyl-1-methylethylamino, 1-cyclopentyl-1-methylethylamino, 1-(1-cyclopentenyl)-1-methylethylamino, 1-cyclohexyl-1-methylethylamino, 1-(1-cyclohexenyl)-1-methylethylamino, 1-methyl-1phenylethylamino, 1,1-dimethyl-2-chloroethylamino, 1,1-dimethyl-3-chloropropylamino, 1,1-dimethyl-2-methoxyethylamino, 1,1-dimethyl-2-(methylamino)ethylamino, 1,1-dimethyl-2-(dimethylamino)ethylamino, and 1,1-dimethyl-3-chloro-2-propenylamino. Any of these groups may also have a methyl substitution on the nitrogen, as in N-(methyl)-1,1-dimethylethylamino and N-(methyl)-1,1-dimethylpropylamino. Of these examples of B, 1,1-dimethylethylamino and N-(methyl)-1,1-dimethylethylamino are preferred.

Further examples of B include 1,1-dimethylethoxy, 1,1-dimethylpropoxy, 1,1-dimethylbutoxy, 1,1-dimethylpentoxy, 1-ethyl-1-methylbutoxy, 2,2-dimethylpropoxy, 2,2-dimethylbutoxy, 1-methyl-1-ethylpropoxy, 1,1-diethylpropoxy, 1,1,2-trimethylpropoxy, 1,1,2-trimethylbutoxy, 1,1,2,2-tetramethylpropoxy, 1,1-dimethyl-2-propenoxy, 1,1,2-trimethyl-2-propenoxy, 1,1-dimethyl-2-butenoxy, 1,1-dimethyl-2-propynyloxy, 1,1-dimethyl-2-butynyloxy, 1-cyclopropyl-1-methylethoxy, 1-cyclobutyl-1-methylethoxy, 1-cyclopentyl-1-methylethoxy, 1-(1-cyclopentenyl)-1-methylethoxy, 1-cyclohexyl-1-methylethoxy, 1-(1-cyclohexenyl)-1-methylethoxy, 1-methyl-1-phenylethoxy, 1,1-dimethyl-2-chloroethoxy, 1,1-dimethyl-3-chloropropoxy, 1,1-dimethyl-2-methoxyethoxy, 1,1-dimethyl-2-(methylamino)ethoxy, 1,1-dimethyl-2-(dimethylamino)ethoxy, 1,1-dimethyl-3-chloro-2-propenoxy. Of these examples of B, 1,1-dimethylethoxy is preferred.

Further examples of B include 1methylcyclopropyl, 1-methylcyclobutyl, 1-methylcyclopentyl, 1-methylcyclohexyl, 1-methylcyclopropylamino, 1-methylcyclobutylamino, 1-methylcyclopentylamino, 1-methylcyclohexylamino, N-(methyl)-1-methylcyclopropylamino, N-(methyl)-1-methylcyclobutylamino, N-(methyl)-1-methylcyclopentylamino, and N-(methyl)-1-methylcyclohexylamino.

$R_n$ may be any substituent(s) which do(es) not unduly reduce the effectiveness of the compounds to function in the method of disease control. Rn is generally a small group; "n" is preferably 1 for benzene rings and 2 for furan and thiophene. R is more preferably methyl or halogen, and more preferably is located adjacent to A.

As used herein, the term "alkyl", unless otherwise indicated, means an alkyl radical, straight or branched chain, having, unless otherwise indicated, from 1 to 10 carbon atoms. The terms "alkenyl" and "alkynyl" mean unsaturated radicals having from 2 to 7 carbon atoms. Examples of such alkenyl groups include ethenyl, 1-propenyl, 2-propenyl, 1-butenyl, 2-butenyl, 3-butenyl, 2-methyl-1-propenyl, 2-methyl-2-propenyl, 1-methylethenyl, and the like. Examples of such alkynyl groups include ethynyl, 1-propynyl, 2-propynyl, 1,1-dimethyl-2-propynyl, and so forth. Substituent groups may also be both alkenyl and alkynyl, for example, 6,6-dimethyl-2-hepten-4-ynyl.

As used herein, the term "alkoxy" means an alkyl group having, unless otherwise indicated, from 1 to 10 carbon atoms connected via an ether linkage. Examples of such alkoxy groups include methoxy, ethoxy, propoxy, 1-methylethoxy, and so forth.

As used herein, the term "alkoxyalkyl" means an ether radical having, unless otherwise indicated, from 1 to 10 carbon atoms. Examples of such alkoxyalkyl groups include methoxymethyl, methoxyethyl, ethoxymethyl, ethoxyethyl, and so forth. As used herein, the terms "monoalkylamino" and "dialkylamino" each mean an amino group having, respectively, 1 or 2 hydrogens replaced with an alkyl group.

As used herein, the term "haloalkyl" means an alkyl radical having one or more hydrogen atoms replaced by halogens, including radicals having all hydrogen atoms substituted by halogen. Examples of such haloalkyl groups are fluoromethyl, difluoromethyl, trifluoromethyl, chloromethyl, trichloromethyl, and so forth.

As used herein, the term "halo" means a radical selected from chloro, bromo, fluoro, and iodo.

Compounds that are useful as the active agent of the present invention include compounds that are described in U.S. Pat. No. 5,811,411 as compounds having the same formula as in Formula (I), above, except:

wherein $Z_1$ and $Z_2$ are C and are part of an aromatic ring which is thiophene;

A is selected from —C(X)-amine, —C(O)—SR$_3$, —NH—C(X)R$_4$, and C(=NR$_3$)—XR$_7$;

B is —W$_m$—Q(R$_2$)$_3$ or selected from o-tolyl, 1-naphthyl, 2-naphthyl, and 9-phenanthryl, each optionally substituted with halogen or R$_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$-$C_4$ alkyl, alkenyl, alkynyl, $C_3$-$C_6$ cycloalkyl, and cycloalkenyl, each optionally substituted with halo, hydroxy, thio, amino, nitro, cyano, formyl, phenyl, $C_1$-$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$-$C_4$ alkyl, alkenyl, alkynyl, alkoxy, alkylthio, alkylamino, dialkylamino, haloalkyl, and haloalkenyl;

d) $C_1$-$C_4$ alkoxy, alkenoxy, alkynoxy, $C_3$-$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino, and further when Q is C, $R_2$ may also be selected from halo, alkoxy, alkylthio, alkylamino, and dialkylamino; and further when Q is C, then two $R_2$ groups may be combined to form a cycloalkyl group with Q;

$R_3$ is $C_1$-$C_4$ alkyl;

$R_4$ is $C_1$-$C_4$ alkyl, haloalkyl, alkoxy, alkylthio, alkylamino, or dialkylamino; $R_7$ is $C_1$-$C_4$ alkyl, haloalkyl, or phenyl, optionally substituted with halo, nitro, or $R_4$;

or an agronomic salt thereof.

Compounds that are useful as the active agent of the present invention include compounds that are described in U.S. Pat. No. 5,998,466 as compounds having the same formula as in Formula (I), above, except:

wherein $Z_1$ and $Z_2$ are C and are part of an aromatic ring which is thiophene;

A is selected from —C(X)-amine, wherein the amine is substituted with a first and a second amine substituent or with an alkylaminocarbonyl and a hydrogen, —C(O)—SR$_3$, —NH—C(X)R$_4$, and —C(=NR$_3$)—XR$_7$;

the first amine substituent is selected from the group consisting of $C_1$-$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, $C_3$-$C_6$ cycloalkyl and $C_5$-$C_6$ cycloalkylkenyl; phenyl optionally substituted with one or more $C_1$-$C_4$ straight or branched alkyl, alkenyl, or alkynyl groups or mixtures thereof, cycloalkyl, cycloalkenyl, haloalkyl, alkoxy and nitro; $C_3$-$C_6$ cycloalkyl, $C_5$-$C_6$ cycloalkenyl, alkoxy, alkenoxy, alkynoxy, dialkylamino, and alkylthio;

and the second amine substituent is selected from the group consisting of hydrogen; $C_1$-$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —$W_m$—$Q(R_2)_3$ or selected from o-tolyl, 1-naphthyl, 2-naphthyl, and 9-phenanthryl, each optionally substituted with halogen or $R_4$;

Q is C, Si, Ge, or Sn;

W is —$C(R_3)_pH_{(2-p)}$—; or when Q is C, W is selected from —$C(R_3)_pH_{(2-p)}$—, —$N(R_3)_mH_{(1-m)}$—, —$S(O)_p$—, and —O—;

X is O or S;

n is 2;

m is 0 or 1;

p is 0, 1, or 2;

wherein two R groups are combined to form a nonheterocyclic ring fused with the thiophene ring, which is not a benzothiophene other than a tetrahydrobenzothiophene, said two R groups being selected from the group consisting of $C_1$-$C_4$ alkyl, alkenyl, $C_3$-$C_6$ cycloalkyl and cycloalkenyl, each optionally substituted with hydroxy, thio, phenyl, $C_1$-$C_4$ alkoxy, alkylthio, alkylsulfinyl, or alkylsufonyl;

each $R_2$ is independently selected from alkyl, alkenyl, alkynyl, cycloalkyl, cycloalkenyl and phenyl, each optionally substituted with $R_4$ or halogen; and wherein when Q is C, $R_2$ may also be selected from halo, alkoxy, alkylthio, alkylamino, and dialkylamino; and further when Q is C, then two $R_2$ groups may be combined to form a cycloalkyl group with Q;

$R_3$ is $C_1$-$C_4$ alkyl;

$R_4$ is $C_1$-$C_4$ alkyl, haloalkyl, alkoxy, alkylthio, alkylamino, or dialkylamino; and $R_7$ is $C_1$-$C_4$ alkyl, haloalkyl, or phenyl, optionally substituted with halo, nitro, or $R_4$;

or an agronomic salt thereof.

Compounds that are useful as the active agent of the present invention include compounds that are described in U.S. Pat. No. 5,834,447 as compounds having the same formula as in Formula (I), above, except:

wherein $Z_1$ and $Z_2$ are C and are part of an aromatic ring which is thiophene;

A is —C(X)-amine wherein the amine is an N-bonded heterocyclic compound chosen from the group consisting of morpholine, piperazine, piperidine, and pyrrolidine, each optionally substituted with $C_3$-$C_6$ alkyl groups;

B is —$W_m$—$Q(R_2)_3$ or selected from o-tolyl, 1-naphthyl, 2-naphthyl, and 9-phenanthryl, each optionally substituted with halogen or $R_4$;

Q is C or Si;

W is —$C(R_3)_pH_{(2-p)}$—; or when Q is C, W is selected from —$C(R_3)_pH_{(2-p)}$—, —$N(R_3)_mH_{(1-m)}$—, —$S(O)_p$—, and —O—;

X is O;

n is 2;

m is 0 or 1;

p is 0, 1, or 2;

wherein the two R groups are alkenyl groups and are combined to form a fused ring with the thiophene ring with is benzothiophene; wherein the alkenyl groups are optionally substituted with halo, hydroxy, thio, amino, nitro, cyano, formyl, phenyl, $C_2$-$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

each $R_2$ is independently selected from alkyl, alkenyl, alkynyl, cycloalkyl, cycloalkenyl, and phenyl, each optionally substituted with $R_4$ or halogen; and wherein when Q is C, $R_2$ may also be selected from halo, alkoxy, alkylthio, alkylamino, and dialkylamino; or wherein two $R_2$ groups may be combined to form a cyclo group with Q;

$R_3$ is $C_1$-$C_4$ alkyl; and $R_4$ is $C_1$-$C_4$ alkyl, haloalkyl, alkoxy, alkylthio, alkylamino, or dialkylamino;

or an agronomic salt thereof

Compounds that are useful as the active agent of the present invention include compounds that are described in U.S. Pat. No. 5,498,630 as compounds having the same formula as in Formula (I), above, except:

wherein $Z_1$ and $Z_2$ are C and are part of an aromatic ring which is benzothiophene; and A is selected from —C(X)-amine wherein the amine is an unsubstituted, monosubstituted or disubstituted nonheterocyclic amino radical, —C(O)—$SR_3$, —NH—$C(X)R_4$, and —C(=$NR_3$)—$XR_7$;

B is —$W_m$—$Q(R_2)_3$ or selected from o-tolyl, 1-naphthyl, 2-naphthyl, and 9-phenanthryl, each optionally substituted with halogen or $R_4$;

Q is C, Si, Ge, or Sn;

W is —$C(R_3)_pH_{(2-p)}$—; or when Q is C, W is selected from —$C(R_3)_pH_{(2-p)}$—, —$N(R_3)_mH_{(1-m)}$—, —$S(O)_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$-$C_4$ alkyl, alkenyl, alkynyl, $C_3$-$C_6$ cycloalkyl, and cycloalkenyl, each optionally substituted with halo, hydroxy, thio, amino, nitro, cyano, formyl, phenyl, $C_1$-$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$-$C_4$ alkyl, alkenyl, alkynyl, alkoxy, alkylthio, alkylamino, dialkylamino, haloalkyl, and haloalkenyl;

d) $C_1$-$C_4$ alkoxy, alkenoxy, alkynoxy, $C_3$-$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with Q which is 1-methylcyclopropyl, 1-methylcyclopentyl, or 1-methylcyclohexyl;

$R_3$ is $C_1$-$C_4$ alkyl;

$R_4$ is $C_1$-$C_4$ alkyl, haloalkyl, alkoxy, alkylthio, alkylamino, or dialkylamino; and $R_7$ is $C_1$-$C_4$ alkyl, haloalkyl, or phenyl, optionally substituted with halo, nitro, or $R_4$;

or an agronomic salt thereof.

Compounds that are useful as the first fungicide of the present invention include compounds that are described in U.S. Pat. No. 5,693,667 as compounds having the same formula as in Formula (I), above, except:

wherein $Z_1$ and $Z_2$ are C or N and are part of an aromatic ring which is furan; and A is selected from —C(X)-amine wherein the amine is substituted with a first and a second amine substituent or with an alkylaminocarbonyl and a hydrogen, —C(O)—$SR_3$, —NH—C(X)$R_4$, and —C(=$NR_3$)—$XR_7$;

the first amine substituent is selected from the group consisting of $C_1$-$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, a 5-membered heteroaryl, $C_3$-$C_6$ cycloalkyl and $C_5$-$C_6$ cycloalkylkenyl; phenyl optionally substituted with one or more $C_1$-$C_4$ straight or branched alkyl, alkenyl, or alkynyl groups or mixtures thereof, cycloalkyl, cycloalkenyl, haloalkyl, alkoxy and nitro; $C_3$-$C_6$ cycloalkyl, $C_5$-$C_6$ cycloalkenyl, alkoxy, alkenoxy, alkynoxy, dialkylamino, and alkylthio;

and the second amine substituent is selected from the group consisting of hydrogen; $C_1$-$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —$W_m$—Q($R_2$)$_3$ or selected from o-tolyi, 1-naphthyl, 2-naphthyl, and 9-phenanthryl, each optionally substituted with halogen or $R_4$;

Q is C, Si, Ge, or Sn;

W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;

X is O or S;

n is 0, 1, or 2;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$-$C_4$ alkyl, alkenyl, alkynyl, $C_3$-$C_6$ cycloalkyl, and cycloalkenyl, each optionally substituted with halo, hydroxy, thio, amino, nitro, cyano, formyl, phenyl, $C_1$-$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$-$C_4$ alkyl, alkenyl, alkynyl, alkoxy, alkylthio, alkylamino, dialkylamino, haloalkyl, and haloalkenyl;

d) $C_1$-$C_4$ alkoxy, alkenoxy, alkynoxy, $C_3$-$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with Q which is 1-methylcyclopropyl, 1-methylcyclopentyl, or 1-methylcyclohexyl;

$R_3$ is $C_1$-$C_4$ alkyl;

$R_4$ is $C_1$-$C_4$ alkyl, haloalkyl, alkoxy, alkylthio, alkylamino, or dialkylamino; and $R_7$ is $C_1$-$C_4$ alkyl, haloalkyl, or phenyl, optionally substituted with halo, nitro, or $R_4$;

or an agronomic salt thereof.

Compounds that are useful as the active agent of the present invention include compounds that are described in U.S. Pat. No. 5,498,630 as compounds having the same formula as in Formula (I), above, except:

wherein $Z_1$ and $Z_2$ are C and are part of an aromatic ring which is benzothiophene; and A is selected from —C(X)-amine wherein the amine is an unsubstituted, monosubstituted or disubstituted nonheterocyclic amino radical, —C(O)—$SR_3$, —NH—C(X)$R_4$, and —C(=$NR_3$)—$XR_7$;

B is —$W_m$—Q($R_2$)$_3$ or selected from o-tolyl, 1-naphthyl, 2-naphthyl, and 9-phenanthryl, each optionally substituted with halogen or $R_4$;

Q is C, Si, Ge, or Sn;

W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$-$C_4$ alkyl, alkenyl, alkynyl, $C_3$-$C_6$ cycloalkyl, and cycloalkenyl, each optionally substituted with halo, hydroxy, thio, amino, nitro, cyano, formyl, phenyl, $C_1$-$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$-$C_4$ alkyl, alkenyl, alkynyl, alkoxy, alkylthio, alkylamino, dialkylamino, haloalkyl, and haloalkenyl;

d) $C_1$-$C_4$ alkoxy, alkenoxy, alkynoxy, $C_3$-$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with Q which is 1-methylcyclopropyl, 1-methylcyclopentyl, or 1-methylcyclohexyl;

$R_3$ is $C_1$-$C_4$ alkyl;

$R_4$ is $C_1$-$C_4$ alkyl, haloalkyl, alkoxy, alkylthio, alkylamino, or dialkylamino; and $R_7$ is $C_1$-$C_4$ alkyl, haloalkyl, or phenyl, optionally substituted with halo, nitro, or $R_4$;

or an agronomic salt thereof.

Compounds that are useful as the active agent of the present invention include compounds that are described in U.S. Pat. No. 5,693,667 as compounds having the same formula as in Formula (I), above, except:

wherein $Z_1$ and $Z_2$ are C and are part of an aromatic ring which is furan; and A is selected from —C(X)-amine wherein the amine is substituted with a first and a second amine substituent or with an alkylaminocarbonyl and a hydrogen, —C(O)—$SR_3$, —NH—C(X)$R_4$, and —C(=$NR_3$)—$XR_7$;

the first amine substituent is selected from the group consisting of $C_1$-$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, a 5-membered heteroaryl, $C_3$-$C_6$ cycloalkyl and $C_5$-$C_6$ cycloalkylkenyl; phenyl optionally substituted with one or more $C_1$-$C_4$ straight or branched alkyl, alkenyl, or alkynyl groups or mixtures thereof, cycloalkyl, cycloalkenyl, haloalkyl, alkoxy and nitro; $C_3$-$C_6$ cycloalkyl, $C_5$-$C_6$ cycloalkenyl, alkoxy, alkenoxy, alkynoxy, dialkylamino, and alkylthio;

and the second amine substituent is selected from the group consisting of hydrogen; $C_1$-$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —$W_m$—Q($R_2$)$_3$ or selected from o-tolyl, 1-naphthyl, 2-naphthyl, and 9-phenanthryl, each optionally substituted with halogen or $R_4$;

Q is C, Si, Ge, or Sn;

W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;

X is O or S;

n is 0, 1, or 2;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$-$C_4$ alkyl, alkenyl, alkynyl, $C_3$-$C_6$ cycloalkyl, and cycloalkenyl, each optionally substituted with halo, hydroxy, thio, amino, nitro, cyano, formyl, phenyl, $C_1$-$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$-$C_4$ alkyl, alkenyl, alkynyl, alkoxy, alkylthio, alkylamino, dialkylamino, haloalkyl, and haloalkenyl;

d) $C_1$-$C_4$ alkoxy, alkenoxy, alkynoxy, $C_3$-$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with Q which is 1-methylcyclopropyl, 1-methylcyclopentyl, or 1-methylcyclohexyl;

$R_3$ is $C_1$-$C_4$ alkyl;

$R_4$ is $C_1$-$C_4$ alkyl, haloalkyl, alkoxy, alkylthio, alkylamino, or dialkylamino; and $R_7$ is $C_1$-$C_4$ alkyl, haloalkyl, or phenyl, optionally substituted with halo, nitro, or $R_4$;

or an agronomic salt thereof.

Compounds that are useful as the active agent of the present invention include compounds that are described in U.S. Pat. No. 5,705,513 as compounds having the same formula as in Formula (I), above, except:

wherein $Z_1$ and $Z_2$ are C and are part of an aromatic ring which is pyridine; and A is selected from the group consisting of —C(O)—$SR_3$, —NH—C(X)$R_4$, and —C(=$NR_3$)—$XR_7$ and —C(X)-amine wherein the amine is substituted with alkylaminocarbonyl and a hydrogen or wherein the amine has a first and a second amine substituent;

the first amine substituent is selected from the group consisting of $C_1$-$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, a 5-membered heteroaryl, $C_3$-$C_6$ cycloalkyl and $C_5$-$C_6$ cycloalkylkenyl; phenyl optionally substituted with one or more $C_1$-$C_4$ straight or branched alkyl, alkenyl, or alkynyl groups or mixtures thereof, cycloalkyl, cycloalkenyl, haloalkyl, alkoxy and nitro; $C_3$-$C_6$ cycloalkyl, $C_5$-$C_6$ cycloalkenyl, alkoxy, alkenoxy, alkynoxy, dialkylamino, and alkylthio;

and the second amine substituent is selected from the group consisting of hydrogen; $C_1$-$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —$W_m$—Q($R_2$)$_3$ or selected from o-tolyl, 1-naphthyl, 2-naphthyl, and 9-phenanthryl, each optionally substituted with halogen or $R_4$;

Q is C, Si, Ge, or Sn;

W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;

X is O or S;

n is 0, 1, or 2;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$-$C_4$ alkyl, alkenyl, alkynyl, $C_3$-$C_6$ cycloalkyl, and cycloalkenyl, each optionally substituted with halo, hydroxy, thio, amino, nitro, cyano, formyl, phenyl, $C_1$-$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$-$C_4$ alkyl, alkenyl, alkynyl, alkoxy, alkylthio, alkylamino, dialkylamino, haloalkyl, and haloalkenyl;

d) $C_1$-$C_4$ alkoxy, alkenoxy, alkynoxy, $C_3$-$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino; or wherein two $R_2$ groups may be combined to form a cyclo group with Q which is 1-methylcyclopropyl, 1-methylcyclopentyl, or 1-methylcyclohexyl;

$R_3$ is $C_1$-$C_4$ alkyl;

$R_4$ is $C_1$-$C_4$ alkyl, haloalkyl, alkoxy, alkylthio, alkylamino, or dialkylamino; and $R_7$ is $C_1$-$C_4$ alkyl, haloalkyl, or phenyl, optionally substituted with halo, nitro, or $R_4$;

or an agronomic salt thereof.

Compounds that are useful as the active agent of the present invention include compounds that are described in U.S. Pat. No. 5,849,723 as compounds having the same formula as in Formula (I), above, except:

wherein $Z_1$ and $Z_2$ are C and are part of an aromatic ring which is benzene; and A is selected from the group consisting of —C(X)-amine wherein the amine is substituted with a first and a second amine substituent or with an alkylaminocarbonyl and a hydrogen; —C(O)—SR_3, —NH—C(X)R_4, and —C(=NR_3)—XR_7;

the first amine substituent is selected from the group consisting of $C_1$-$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, $C_3$-$C_6$ cycloalkyl and $C_5$-$C_6$ cycloalkylkenyl; phenyl optionally substituted with one or more $C_1$-$C_4$ straight or branched alkyl, alkenyl, or alkynyl groups or mixtures thereof, cycloalkyl, cycloalkenyl, haloalkyl, alkoxy and nitro; $C_3$-$C_6$ cycloalkyl, $C_5$-$C_6$ cycloalkenyl, alkoxy, alkenoxy, alkynoxy, dialkylamino, and alkylthio;

and the second amine substituent is selected from the group consisting of hydrogen; $C_1$-$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —$W_m$—$Q(R_2)_3$ or selected from o-tolyl, 1-naphthyl, 2-naphthyl, and 9-phenanthryl, each optionally substituted with halogen or $R_4$;

Q is Si, Ge, or Sn;

W is —$C(R_3)_pH_{(2-p)}$—;

X is O or S;

n is 0, 1, 2 or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$-$C_4$ alkyl, alkenyl, alkynyl, $C_3$-$C_6$ cycloalkyl, and cycloalkenyl, each optionally substituted with halo, hydroxy, thio, amino, nitro, cyano, formyl, phenyl, $C_1$-$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$-$C_4$ alkyl, alkenyl, alkynyl, alkoxy, alkylthio, alkylamino, dialkylamino, haloalkyl, and haloalkenyl;

d) $C_1$-$C_4$ alkoxy, alkenoxy, alkynoxy, $C_3$-$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each $R_2$ is independently selected from alkyl, alkenyl, alkynyl, cycloalkyl, cycloalkenyl and phenyl, each optionally substituted with $R_4$ or halogen;

$R_3$ is $C_1$-$C_4$ alkyl;

$R_4$ is $C_1$-$C_4$ alkyl, haloalkyl, alkoxy, alkylthio, alkylamino, or dialkylamino; and $R_7$ is $C_1$-$C_4$ alkyl, haloalkyl, or phenyl, optionally substituted with halo, nitro, or $R_4$;

or an agronomic salt thereof.

Compounds that are useful as the active agent of the present invention include compounds that are described in U.S. Pat. No. 6,028,101 as compounds having the same formula as in Formula (I), above, except:

wherein $Z_1$ and $Z_2$ are C and are part of an aromatic ring which is furan; and A is selected from —C(X)-amine wherein the amine is substituted with a first and a second amine substituent or with an alkylaminocarbonyl and a hydrogen, —C(O)—SR_3, —NH—C(X)R_4, and —C(=NR_3)—XR_7;

the first amine substituent is selected from the group consisting of $C_1$-$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, a 5-membered heteroaryl, $C_3$-$C_6$ cycloalkyl and $C_5$-$C_6$ cycloalkylkenyl; phenyl optionally substituted with one or more $C_1$-$C_4$ straight or branched alkyl, alkenyl, or alkynyl groups or mixtures thereof, cycloalkyl, cycloalkenyl, haloalkyl, alkoxy and nitro; $C_3$-$C_6$ cycloalkyl, $C_5$-$C_6$ cycloalkenyl, alkoxy, alkenoxy, alkynoxy, dialkylamino, and alkylthio;

and the second amine substituent is selected from the group consisting of hydrogen; $C_1$-$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —$W_m$—$Q(R_2)_3$ or selected from o-tolyl, 1-naphthyl, 2-naphthyl, and 9-phenanthryl, each optionally substituted with halogen or $R_4$;

Q is C, Si, Ge, or Sn;

W is —$C(R_3)_pH_{(2-p)}$—; or when Q is C, W is selected from —$C(R_3)_pH_{(2-p)}$—, —$N(R_3)_mH_{(1-m)}$—, —$S(O)_p$—, and —O—;

X is O or S;

n is 2;

m is 0 or 1;

p is 0, 1, or 2;

wherein the two R groups are combined to form a nonheterocyclic ring fused to said furan ring which is not benzofuran when A is —C(X)-amine, B is —Wm(Q)—(R_2)_3, and Q is C or Si, said R groups being selected from the group consisting of $C_1$-$C_4$ alkyl, alkenyl, $C_3$-$C_6$ cycloalkyl and cycloalkenyl, each optionally substituted with hydroxy, thio, phenyl, $C_1$-$C_4$ alkoxy, alkylthio, alkylsulfinyl, or alkylsulfonyl; and each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino; wherein further when Q is C, then two $R_2$ groups may be combined to form a cyclo group with Q;

$R_3$ is $C_1$-$C_4$ alkyl;

$R_4$ is $C_1$-$C_4$ alkyl, haloalkyl, alkoxy, alkylthio, alkylamino, or dialkylamino; and $R_7$ is $C_1$-$C_4$ alkyl, haloalkyl, or phenyl, optionally substituted with halo, nitro, or $R_4$;

or an agronomic salt thereof.

Compounds that are useful as the active agent in the present invention can also be selected from those described in U.S. Pat. No. 5,482,974, namely, a compound having the formula

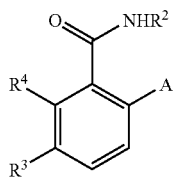

wherein $R^2$ is ethyl, iso-propyl, propyl or allyl;

A is $N(CH_3)_{1-n}H_nR^5$ or $OR^6$ wherein n is 0 or 1, $R^5$ is $(CH_3)_m(CH_3CH_2)_{3-m}C$, 1-methyl-1-cyclopentyl, 1-methyl-1-cyclohexyl or 2,3-dimethyl-2-butyl wherein m is 0, 1, 2 or 3 and $R^6$ is independently $R^5$, or 2,3,3-trimethyl-2-butyl;

$R^3$ is H or independently $R^4$; and $R^4$ is halo or $CH_3$;

with the proviso that when A is $N(CH_3)_{1-n}H_nR^5$, if $R^3$ is H and $R^5$ is 1-methyl-1-cyclohexyl or $(CH_3)_m(CH_2CH_3)_{3-m}C$, where m is 0 or 3, or if $R^3$ is halo and $R^2$ is $(CH_3)_m(CH_3CH_2)_{3-m}C$, where m is 3, then $R^2$ cannot be ethyl;

and with the proviso that when A is $OR^6$ then m is equal to or less than 2, and if $R^3$ is H or halo and $R^2$ is ethyl or isopropyl, then $R^6$ is $(CH_3)_M(CH_3CH_2)_{3-M}C$ where m is 1;

or an agronomic salt thereof.

Compounds that are useful as the active agent in the present invention can also be selected from those described in U.S. Pat. No. 5,994,270, namely, a compound having the formula:

(a)
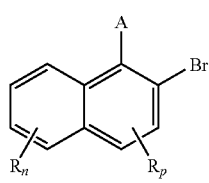

(b)
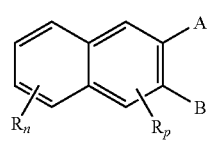

(c)
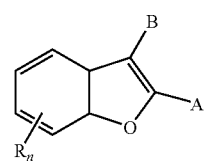

(d)
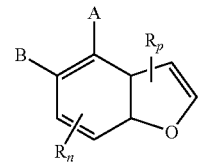

(e)
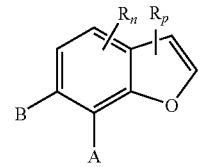

(f)
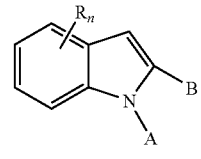

(g)
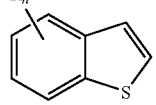

(h)
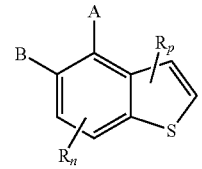

(i)
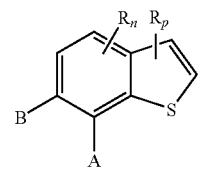

(j)
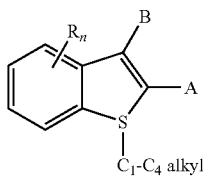

where A is —C(X)-amine; B is —$W_m$—$Q(R_2)_3$; and A can be B when B is A except when the formula is f),then Q cannot be Si;

Q is C or Si;

W is —NH—, —O— or $NCH_3$—;

X is O or S;

m is 0 or 1, provided that m is 0 when Q is Si;

n is 0, 1, 2, or 3 p is 0, 1 or 2, and n plus p is equal to or less than 3; each R is independently selected from a) halo, formyl, cyano, amino, nitro, thiocyanato, isothiocyanato, trimethylsilyl, and hydroxy;

b) $C_1$-$C_4$ alkyl, alkenyl, alkynyl, $C_3$-$C_6$ cycloalkyl, and cycloalkenyl, each optionally substituted with halo, hydroxy, thio, amino, nitro, cyano, formyl, phenyl, $C_1$-$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$-$C_4$ alkyl, alkenyl, alkynyl, alkoxy, alkylthio, alkylamino, dialkylamino, haloalkyl, and haloalkenyl;

d) $C_1$-$C_4$ alkoxy, alkenoxy, alkynoxy, $C_3$-$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo; each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino; wherein two $R_2$ groups may be combined to form a cyclo group with Q; $R_4$ is $C_1$-$C_4$ alkyl, haloalkyl, alkoxy, alkylthio, alkylamino, or dialkylamino; or an agronomic salt thereof.

A preferred active agent is a compound having the structure:

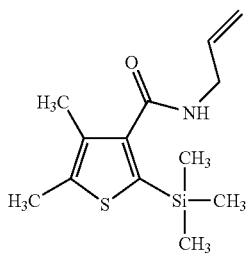

and which has a CAS name of 4,5-dimethyl-N-(2-propenyl)-2-(trimethylsilyl)-3-thiophenecarboxamide, having a CAS registration number of 175217-20-6, and for which the ISO common name is silthiofam. Further information about silthiofam can be found in U.S. Pat. No. 5,486,621.

The active agent of the present invention can be used in any purity that passes for such agent in the commercial trade. The agent can be used in any form in which it is received from the supplier, or in which it is synthesized. It is preferred that the active agent be supplied in a liquid form. However, the liquid can be a substantially pure form of the agent, or it can be the agent dissolved in a solvent. Commonly, if a solvent is present, such solvents are organic liquid solvents that are commonly used in such applications. If the active agent is water soluble, then water can be used as the solvent.

The treatment of a plant or propagation material, such as a seed, with an active agent by the method of this invention can be accomplished in several ways. The agent may be applied directly to the seed and/or to soil in which the seed is to be planted, for example, at the time of planting along with the seed. Alternatively, it may be applied to the soil after planting and germination, or to the foliage of the plant after emergence.

When it is said that "an effective amount" of a fungicide or other active agent is used in the subject method, it is meant that a sufficient amount of the fungicide or other active agent is applied to the plant or its propagation material to achieve an increase in the yield and/or the vigor of the plant. The amount of the active agents that are useful in the subject method will be discussed in more detail below.

Compositions for soil application include clay granules which may be applied in-furrow, as broadcast granules or as impregnated fertilizer granules. In addition, the agent may be applied to the soil as a preemergent or postemergent spray, or to the plant as a postemergent spray.

In one embodiment, the agent is applied to the seed in a treatment prior to planting. One method of carrying out such treatment is to apply a coating containing the active agent to the seed. This technique is commonly used in many crops to provide fungicides for control of various phytopathological fungi.

When the seed is treated prior to planting with a composition that contains the active agent, it can be treated with an amount of the composition sufficient to include the active agent in an amount that is within the range of about 0.1 gm/100 kg of seed to about 500 gm/100 kg of seed. It is preferred that the active agent be applied to the seed in an amount that is within the range of about 2 gm/100 kg and about 200 gm/100 kg, more preferred that it be applied in an amount of from about 10 gm/100 kg of seed to about 100 gm/100 kg of seed, and a range of about 20 gm/100 kg to about 50 gm/100 kg of seed is yet more preferred.

Plants and/or seed to be treated by the subject method can be treated with one or more forms of the useful active agents without any additional materials being present. However, in some cases, it is preferred to use the one or more active agents in combination with other materials in a composition.

Compositions of the present invention are comprised of an effective amount of one or more of the active agents described above and one or more adjuvants. If desirable, such compositions can also include such other materials as herbicides, pesticides—such as insecticides, nematicides, acaricides, fungicides, and the like, growth factors, fertilizers, and any other material that will provide a desirable feature for protecting, sprouting and growing the plant, and/or for improving the yield or vigor of the plant. The choice of such other materials will depend on the crop and the diseases known to be a threat to that crop in the location of interest. In one embodiment, the active agent can be combined with a herbicide for foliar application to the plant. Any of the active agents discussed above can be used in this combination, but silthiopham is a preferred active agent.

When a herbicide is used with the active agent, any herbicide can be used, provided that the plant that is to be treated has resistance to such herbicide. As described above, it is preferred that the plant have a transgenic event providing the plant with resistance to the herbicide being used. Within these limitations, any herbicide can be used in the combination and useful herbicides include, without limitation, imidazolinone, acetochlor, acifluorfen, aclonifen, acrolein, AKH-7088, alachlor, alloxydim, ametryn, amidosulfuron, amitrole, ammonium sulfamate, anilofos, asulam, atrazine, azafenidin, azimsulfuron, BAS 620H, BAS 654 00 H, BAY FOE 5043, benazolin, benfluralin, benfuresate, bensulfuron-methyl, bensulide, bentazone, benzofenap, bifenox, bilanafos, bispyribac-sodium, bromacil, bromobutide, bromofenoxim, bromoxynil, butachlor, butamifos, butralin, butroxydim, butylate, cafenstrole, carbetamide, carfentrazone-ethyl, chlormethoxyfen, chioramben, chlorbromuron, chioridazon, chiorimuron-ethyl, chloroacetic acid, chiorotoluron, chlorpropham, chlorsulfuron, chlorthal-dimethyl, chlorthiamid, cinmethylin, cinosulfuron, clethodim, clodinafop-propargyl, clomazone, clomeprop, clopyralid, cloransulam-methyl, cyanazine, cycloate, cyclosulfamuron, cycloxydim, cyhalofop-butyl, 2,4-D, daimuron, dalapon, dazomet, 2,4DB, desmedipham, desmetryn, dicamba, dichiobenil, dichiorprop, dichlorprop-P, diclofop-methyl, difenzoquat metilsulfate, diflufenican, dimefuron, dimepiperate, dimethachlor, dimethametryn, dimethenamid, dimethipin, dimethylarsinic acid, dinitramine, dinocap, dinoterb, diphenamid, diquat dibromide, dithiopyr, diuron, DNOC, EPTC, esprocarb, ethaifluralin, ethametsulfuron-methyl, ethofumesate, ethoxysulfuron, etobenzanid, fenoxaprop-P-ethyl, fenuron, ferrous sulfate, flamprop-M, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, flupropanate, flupyrsulfuron-methyl-sodium, flurenol, fluridone, flurochloridone, fluroxypyr, flurtamone, fluthiacet-methyl, fomesafen, fosamine, giufosinate-ammonium, glyphosate, glyfosinate, halosulfuron-methyl, haloxyfop, HC-252, hexazinone, imazamethabenz- methyl, imazamox, imazapyr, imazaquin, imazethapyr, imazosuluron, imidazilinone, indanofan, ioxynil, isoproturon, isouron, isoxaben, isoxaflutole, lactofen, lenacil,linunuron, MCPA, MCPA-thioethyl, MCPB, mecoprop, mecoprop-P, mefenacet, metamitron, metazachlor, methabenzthiazuron, methylarsonic acid, methyldymron, methyl isothiocyanate, metobenzuron, metobromuron, metolachior, metosulam, metoxuron, metribuzin, metsulfuron-methyl, molinate, monolinuron, naproanilide, napropamide, naptalam, neburon, nicosulfuron, nonanoic acid, norflurazon, oleic acid (fatty acids), orbencarb, oryzalin, oxadiargyl, oxadiazon, oxasulfuron, oxyfluorfen, paraquat dichioride, pebulate, pendimethalin, pentachlorophenol, pentanochlor, pentoxazone petroleum oils, phenmedipham, picloram, piperophos, pretilachlor, primisulfuron-methyl, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, pyrithiobac-sodium, quinclorac, quinmerac, quinoclamine, quizalofop, quizalofop-P, rimsulfuron, sethoxydim, siduron, simazine, simetryn, sodium chlorate, STS system (sulfonylurea), sulcotrione, sulfentrazone, sulfometuron-methyl, sulfosulfuron, sulfuric acid, tar oils, 2,3,6-TBA, TCA-sodium, tebutam, tebuthiuron, terbacil, terbumeton, terbuthylazine, terbutryn, thenylchlor, thiazopyr, thifensu lfuron-methyl, thiobencarb, tiocarbazil, tralkoxydim, tri-allate, triasulfuron, triaziflam, tribenuronmethyl, triclopyr, trietazine, trifluralin, triflusu lfuron-methyl, and vernolate.

Preferred herbicides include glyphosate, glufosinate, imidazolinone herbicides, and sulfonylurea herbicides.

When the active agent is 4,5-dimethyl-N-(2-propenyl)-2-(trimethylsilyl)-3-thiophenecarboxamide (silthiopham), a preferred herbicide is glyphosate, (N-(phosphonomethyl) glycine).

The active agent can be combined with a fungicide to treat seed or for foliar application. Any fungicide can be used and examples of useful fungicides include fludioxonil, fluquinconazole, captan, metalaxyl, carboxin, thiram, difenoconazole and tebuconazole. When the active agent is used to treat soybeans, the agent can be used for either seed treatment or foliar treatment in combination with fungicides that are commonly used on soybeans, such as captan, metalaxyl, carboxin and thiram.

It is also contemplated that the subject method can include treatment of a seed with an inoculant, followed by foliar treatment with an active agent, or by foliar treatment with an active agent and a herbicide. The subject treatment can also include the treatment of a seed with an inoculant and an active agent, followed by foliar treatment with an active agent and/or a herbicide. In any one of these treatment protocols, other fungicides and/or pesticides can be included at any step of the treatment method.

The active agent may be present in such compositions at levels from 0.01 to 95 percent by weight. Preferably, such compositions contain the active agent in an amount of from about 1% to about 50%, by weight, and more preferably, in an amount of from about 5% to about 25%, by weight.

The compositions of this invention, including concentrates that require dilution prior to application, may contain at least one active agent and an adjuvant in liquid or solid form. The compositions are prepared by admixing the active agent with or without an adjuvant plus diluents, extenders, carriers, and conditioning agents to provide compositions in the form of finely-divided particulate solids, granules, pellets, solutions, dispersions or emulsions. Thus, it is believed the active agent could be used with an adjuvant such as a finely-divided solid, a liquid of organic origin, water, a wetting agent, a dispersing agent, an emulsifying agent or any suitable combination of these.

Agronomically acceptable carriers for active agents are well known and include, for example, solid carriers such as fine powders or granules of kaolin clay, attapulgite clay, bentonite, acid clay, pyrophyllite, talc, diatomaceous earth, calcite, corn starch powder, walnut shell powder, urea, ammonium sulfate, synthetic hydrated silicon dioxide and the like. Acceptable liquid carriers include, for example, aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cottonseed oil, corn oil and the like, dimethyl sulfoxide, acetonitrile, water and the like.

Suitable wetting agents are believed to include alkyl benzene and alkyl naphthalene sulfonates, alkyl and alkyl aryl sulfonates, alkyl amine oxides, alkyl and alkyl aryl phosphate esters, organosilicones, fluoro-organic wetting agents, alcohol ethoxylates, alkoxylated amines, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, block copolymers, polyoxyalkylene derivatives of alkylphenols (particularly isooctylphenol and nonylphenol) and polyoxyalkylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, polymethylene bisnaphthalene sulfonate, and neutralized polyoxyethylated derivatives or ring-substituted alkyl phenol phosphates. Stabilizers may also be used to produce stable emulsions, such as magnesium aluminum silicate and xanthan gum.

Other formulations include dust concentrates comprising from 0.1 to 60% by weight of the active agent on a suitable extender, optionally including other adjuvants to improve handling properties, e.g., graphite. These dusts may be diluted for application at concentrations within the range of from about 0.1-10% by weight.

Concentrates may also be aqueous emulsions, prepared by stirring a non-aqueous solution of a water insoluble active agent and an emulsification agent with water until uniform and then homogenizing to give stable emulsion of very finely divided particles. Or they may be aqueous suspensions, prepared by milling a mixture of a water-insoluble active agent and wetting agents to give a suspension, characterized by its extremely small particle size, so that when diluted, coverage is very uniform. Suitable concentrations of these formulations contain from about 0.1-60% preferably 5-50% by weight of active agent.

Concentrates may be solutions of active agent in suitable solvents together with a surface active agent. Suitable solvents for the active agents of this invention for use in seed treatment include propylene glycol, furfuryl alcohol, other alcohols or glycols, and other solvents that do not substantially interfere with seed germination. If the active agent is to be applied to the soil, then solvents such as N,N-dimethylformamide, dimethylsulfoxide, N-methylpyrrolidone, hydrocarbons, and water immiscible ethers, esters, or ketones are useful.

The concentrate compositions herein generally contain from about 1.0 to 95 parts (preferably 5-60 parts) of the active agent, about 0.25 to 50 parts (preferably 1-25 parts) surface active agent and where required about 4 to 94 parts solvent, all parts being by weight based on the total weight of the concentrate.

The following 125 g/l active agent suspension concentrate of 4,5-dimethyl-N-2-propenyl-2-(trimethylsilyl)-3-thiophene carboxamide may be utilized in accordance with the present invention. Such composition will be referred to as Composition I.

| Ingredient | Amount (g/L) |
| --- | --- |
| 4,5-dimethyl-N-2-propenyl-2-(trimethylsilyl)-3-thiophene carboxamide (96%) | 130.4 |
| Pluronic PE 10500 | 40.0 |
| Polypropylene glycol | 80.0 |
| Polyfon O | 10.0 |
| Permanent Rubine LB6 02 | 30.0 |
| Rhodorsil 432R | 1.0 |
| Orchex 796 | 40.0 |
| Vinamul 18160 | 60.0 |
| Rhodopol 23 | 0.80 |
| Phylatol | 0.32 |
| Water | 641.9 |
| Specific gravity = 1.034 | |

In addition, the following 250 g/l active agent suspension concentrate of silthiopham may be utilized in accordance with the present invention. Such composition will be referred to herein as Composition II.

| Ingredient | Amount g/L |
| --- | --- |
| 4,5-dimethyl-N-2-propenyl-2-(trimethylsilyl)-3-thiophene carboxamide (96%) | 275.5 |
| Pluronic PE 10500 | 35.2 |
| Polypropylene glycol | 71.5 |
| Polyfon O | 10.7 |
| Permanent Rubine LB6 02 | 21.4 |
| Rhodorsil 432R | 0.85 |
| Orchex 796 | 61.9 |
| Vinamul 18160 | 64.1 |
| Rhodopol 23 | 0.75 |
| Panacide M | 0.75 |
| Water | 525.4 |
| Specific gravity = 1.068 (estimated) | |

For application to the soil at the time of planting, a granular formulation may be used. Granules are physically stable particulate compositions comprising at least one active agent adhered to or distributed through a basic matrix of an inert, finely divided particulate extender. In order to aid leaching of the active agent from the particulate, a surface active agent such as those listed hereinbefore, or for example, propylene glycol, can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely divided clays such as kaolin clays, hydrated attapulgite or bentonitic clays. These extenders are sprayed or blended with the active agent to form the granules.

The granular compositions of this invention may contain from about 0.1 to about 30 parts by weight of active agent per 100 parts by weight of clay and 0 to about 5 parts by weight of surface active agent per 100 parts by weight of particulate clay.

The method of the present invention may be carried out by mixing the composition comprising the active agent into the seed prior to planting at rates from 0.01 to 50 g per kg of seed, preferably from 0.1 to 5 g per kg, and more preferably from 0.2 to 2 g per kg. If application to the soil is desired, the compounds may be applied at rates from 1 to 1000 g per hectare, preferably from 10 to 500 g per hectare. The higher application rates will be needed for situations of light soils or greater rainfall or both.

When silthiopham is the active agent, a preferred formulation is a flowable concentrate for seed treatment (FS) that contains from about 115.5 g/l to about 132.6 g/l of silthiopham and, more preferably contains about 125.0 g/l of silthiopham (12.47% wt/wt). A preferred application rate of this composition to seed is at a level of about 25 g/100 kg of seed.

When the active agent is used to treat seeds, it is preferred that an inoculant be used. The inoculant can be any one of the types of inoculant that is known for use with the type of plant that is the subject of treatment. For example, if corn is being treated, the corn seed could be treated with an inoculant containing *Azospirillium* spp. When a legume is being treated, the inoculant can be one that is known for use with legumes. Some examples of inoculants that are used in the culture of legumes are those including *Rhizobium* spp., a *Bradyrhizobium* spp., or a mixture thereof, or a mixture of either of those bacterium with one or more other microorganism strains. Examples of useful inoculants include a *Bradyrhizobium japonicum* inoculant (USDA Soybean Inoculant) produced by Urbana Laboratories of Urbana, Ill.

If an inoculant is used, it can be applied at any time, and at any rate, and by the use of any method of application. When the inoculant is to be used in conjunction with seed that has been treated with the subject active agent, it is preferred that the treated seed be contacted with the inoculant before planting. It is more preferred that the treated seed be contacted with the inoculant within a time before planting that is sufficiently brief so as to minimize any negative effect that the active agent might have on the inoculant. The inoculant can be applied to the treated seeds no more than 24 hours before planting, preferably no more than 10 hours before planting, and more preferably no more than 5 hours before planting.

Alternatively, the inoculant can be applied to the soil surrounding the seed at the time of planting, or it may be administered to the soil at any time after planting. One method of applying the active agent to the soil surrounding the seed at the time of planting is to add the inoculant to the seed furrow at the same time the seed is planted. Any of these methods should be considered to be included when it is mentioned herein that seed is treated with an inoculant.

Although any amount of the inoculant can be added to the seed, it is preferred that the inoculant be added at approximately the rate recommended by its supplier. When the inoculant is provided in the form of a culture of bacterium that is distributed on peat or humus, for example, the inoculant can be applied to the seed at a rate of from about 1 g/kg of seed to about 50 g/kg of seed, and preferably at a rate of about 10 g/kg of seed.

When an inoculant is contacted with seed, a sticking agent can also be used to help to adhere an even coating of the inoculant to each seed. Many such sticking agents are known in the art and any can be used. An example of one sticking agent that can be used is Mollyflo® (available from Soygro (Pty) Ltd., of Mooibank, Botchefstroom, South Africa). When a sticking agent is used, it can be used at any rate, but it is preferred that it is used at the rate that is recommended by its supplier. When Mollyflo® is used, it can be applied to the seed prior to the application of the inoculant at a rate of from about 40 ml/100 kg of seed to about 4,000 ml/100 kg of seed, more preferably at a rate of about 400 ml/100 kg of seed.

The active agents of the present invention can also be applied to seed or to soil in the form of controlled release formulations. Such controlled release formulations are well known in the art and include microparticles, microcapsules, matrix coatings, matrix granules, and the like.

It is believed that the present invention is particularly advantageous when applied to plants or seeds that are, or will become, under some type of stress prior to, during, or after germination. Drought, excessive cold or heat commonly causes such stress, unsuitable nutritional or ionic conditions of the soil, and the like. Accordingly, it is believed that the subject method would be particularly useful for such farming practices as dry-land farming, no-till farming, use of conservative farming practices, early planting, or any other technique or situation which would normally be expected to cause stress on the seeds and/or the plants.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

EXAMPLE 1

This example shows a method of treating soybean seed with silthiofam with and without *Bradyrhizobium* spp. inoculum.

Soybean seed (CSR2121 variety, available from Monsanto Company, St. Louis, Mo.), was placed in a rotostatic seed treatment device (available from Hege Equipment, Inc., Colwich, Kans.). A spreader/sticker compound (Mollyflo®, available from Soygro (Pty) Ltd., Mooibank, Botchefstroom, South Africa) was added to the seed with agitation at the rate of 4 ml/kg of seed and distributed over the eed. A formulation containing 4,5-dimethyl-N-2-propenyl-2-trimethylsilyl)-3-thiophene carboxamide (silthiopham) as the active ingredient was added to the coated seed at the rate of 2 ml/kg of seed. The formulation was prepared according to the formulation shown above for Composition I, and contained about 125 gm/liter of silthiopham. The active formulation was added to the coated seed after addition of the spreader/sticker and during agitation of the seed.

For seeds that were to receive a coating of an inoculant, a peat-based *Bradyrhizobium* spp. formulation was added to the seeds immediately before planting by adding the inoculant formulation to the seed at a rate of 10 gm/kg of seed. The inoculant formulation was added to the seed in a seed packet and thoroughly manually intermixed to contact all of the seed with the inoculant. The seed were then ready for planting.

EXAMPLE 2

This example shows the effect of the treatment of soybean seed with silthiopham on the yield and vigor of soybean plants in a field trial in the United States.

A field trial was carried out in the upper Midwestern United States for the purpose of testing the effect of soybean seed treatment with silthiopham compared to no treatment and seed treatments with conventional materials. The soil type for the site was St. Charles silt loam having a pH of 6.4, and having P=48 ppm, K=154 ppm, and O.M.=3.0%. No fertilizer was applied, and no-tillage cultivation practice was adhered to. The trial followed Roundup-Ready® corn on which Harness® followed by Roundup® and Atrazine® had been applied according to conventional practice. There was no irrigation. The trial was of RCB 1 factor design, with 4 replications. Seeds were planted as early as possible to ensure some stress on the seeds.

Soybean seeds of the CSR2121 variety (available from Monsanto Company, St. Louis, Mo.) were supplied that received the treatments shown in Table 1.

TABLE 1

Soybean seed treatments applied for upper Midwestern United States field trial.

| | AMOUNT OF MATERIAL APPLIED TO THE SEED | | | | |
|---|---|---|---|---|---|
| TREATMENT | Rival (floz/cwt of seed) | Allegiance (floz/cwt of seed) | Mollyflo[a] (ml/kg of seed) | Silthiopham[c] (gm of active ingredient/100 kg of seed) | Bradyrhizobium spp. inoculant[b] (g/kg of seed) |
| Untreated Control (UTC) | 0 | 0 | 0 | 0 | 0 |
| Mollyflo + Inoculant | 0 | 0 | 4.0 | 0 | 10.0 |
| Silthiopham | 0 | 0 | 0 | 2.0 | 0 |
| Silthiopham + Mollyflo + Inoculant | 0 | 0 | 4.0 | 2.0 | 10.0 |

TABLE 1-continued

Soybean seed treatments applied for upper Midwestern United States field trial.

| TREATMENT | AMOUNT OF MATERIAL APPLIED TO THE SEED | | | | |
|---|---|---|---|---|---|
| | Rival (floz/cwt of seed) | Allegiance (floz/cwt of seed) | Mollyflo[a] (ml/kg of seed) | Silthiopham[c] (gm of active ingredient/100 kg of seed) | Bradyrhizobium spp. inoculant[b] (g/kg of seed) |
| Rival + Allegiance[d] | 5.0 | 0.375 | 0 | 0 | 0 |

Notes
[a] Mollyflo ® was applied to seed in a rotostatic seed treatment machine (Hege machine) prior to seed packeting.
[b] Inoculant was added to seed envelopes in the field immediately prior to planting.
[c] In all seeds treated with silthiopham, the silthiopham was added to seed in a rotostatic seed-treating machine prior to the addition of Mollyflo ®.
[d] Rival ® /Allegiance ® were added to seed in a rotostatic seed treating machine prior to planting. Rival ® is a mixture of three fungicides, Allegiance ® is a formulation of metalaxyl. Both are available from Gustafson.

After the seeds had received the designated treatments, they were planted on May 11 in 8-row plots with 15-inch row spacing and in rows of 50-ft. length on a 10'×50' plot. Stand counts were carried out at Vc-V1 (June 1) and at V3 stages (June 21). Plant vigor was reported according to a standard 1-9 scale, with 1 being worst and 9 being best and most vigorous. The percent canopy was reported as percent of canopy closure where 100% is total coverage. Vigor and canopy determinations were made at 50, 60, 71, 82, 92 and 102 days after planting. Days to maturity were counted from planting until 95% pod brown. The plant height, seed yield and seed size were determined at plant maturity. The response of the soybeans to the various treatments is shown in Table 2.

Mollyflo® and inoculant generally performed intermediate to the untreated control and the silthiopham+inoculant in terms of canopy development and plant vigor.

Figure 3:
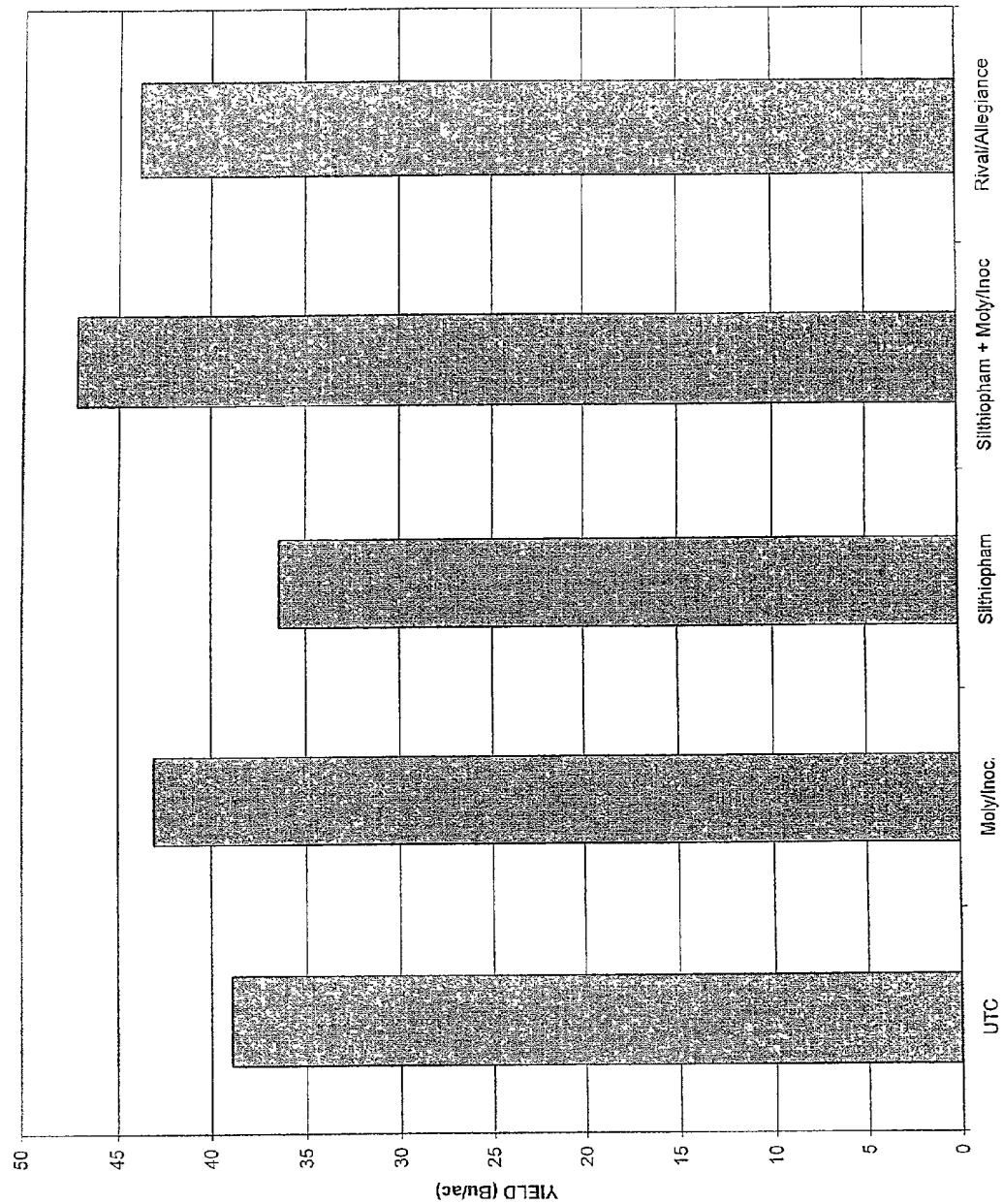
FIG. 3 shows the soybean yield of soybean plants in a field trial for soybeans receiving no treatment prior to planting (UTC) compared with soybeans that had been treated prior to planting with silthiopham (Silthiopham), silthiopham+inoculant (Silthiopham+Moly/Inoc), a sticker+inoculant (Moly/Inoc), and a standard fungicide treatment (Rival/Allegiance)

However, differences were more pronounced for soybean yield and seed weight. As shown in FIG. 3, beans treated with silthiopham+Mollyflo®+inoculant showed over a 20% improvement in yield compared with untreated control beans, while beans receiving only the Mollyflo® and inoculant improved by a little over 10%, and beans receiving Rival®/Allegiance® improved by almost 13%. Beans receiving silthiopham alone showed no improvement over the untreated control, and, in fact, were somewhat below the control level.

TABLE 2

Response of soybeans to various treatments including treatment with and without silthiopham.

| TREATMENT | Grain Yield[b] (bu/ac) | Seed Weight (gm/100 seeds | Plant Height (inches) | Days to Maturity | Vigor (1 worst-9 best) | Canopy (% coverage) |
|---|---|---|---|---|---|---|
| Untreated Control (UTC) | 38.9 | 11.3 | 22.8 | 105.3 | 7 | 79 |
| Mollyflo + Inoculant | 43.1 | 12.0 | 23.0 | 109.5 | 8 | 89 |
| Silthiopham | 36.4 | 11.0 | 22.8 | 106.5 | 6 | 78 |
| Silthiopham + Mollyflo + Inoculant | 47.2 | 12.3 | 26.5 | 106.8 | 9 | 95 |
| Rival + Allegiance[d] | 42.1 | 11.7 | 23.9 | 106.9 | 8 | 94 |

Figure 2:
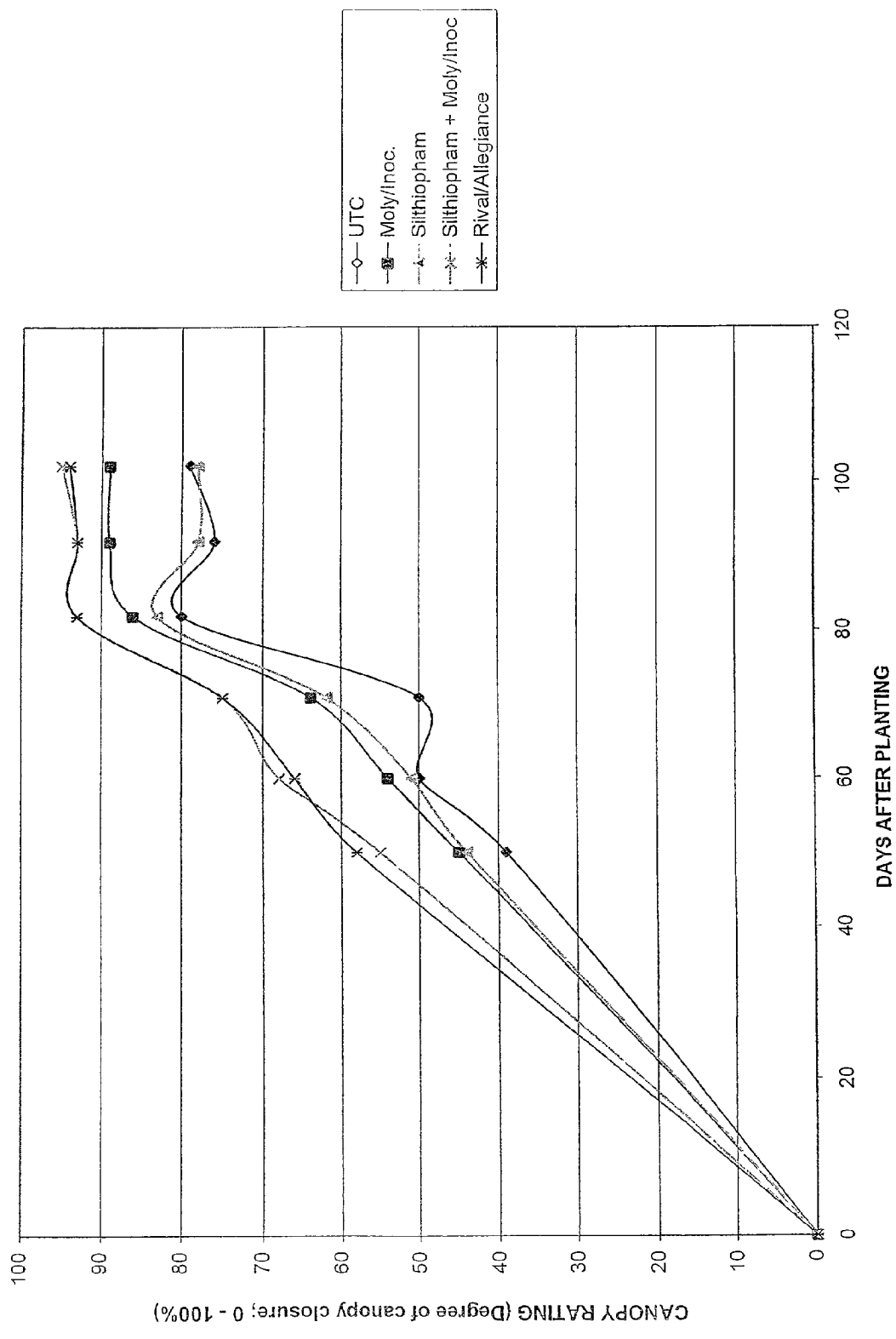
FIG. 2 is a plot of the canopy rating of soybean plants in a field trial as a function of time after planting for soybeans receiving no treatment prior to planting (UTC) compared with soybeans that had been treated prior to planting with silthiopham (Silthiopham), silthiopham+inoculant (Silthiopham+Moly/Inoc), a sticker+inoculant (Moly/inoc), and a standard fungicide treatment (Rival/Allegiance)
Figure 4:
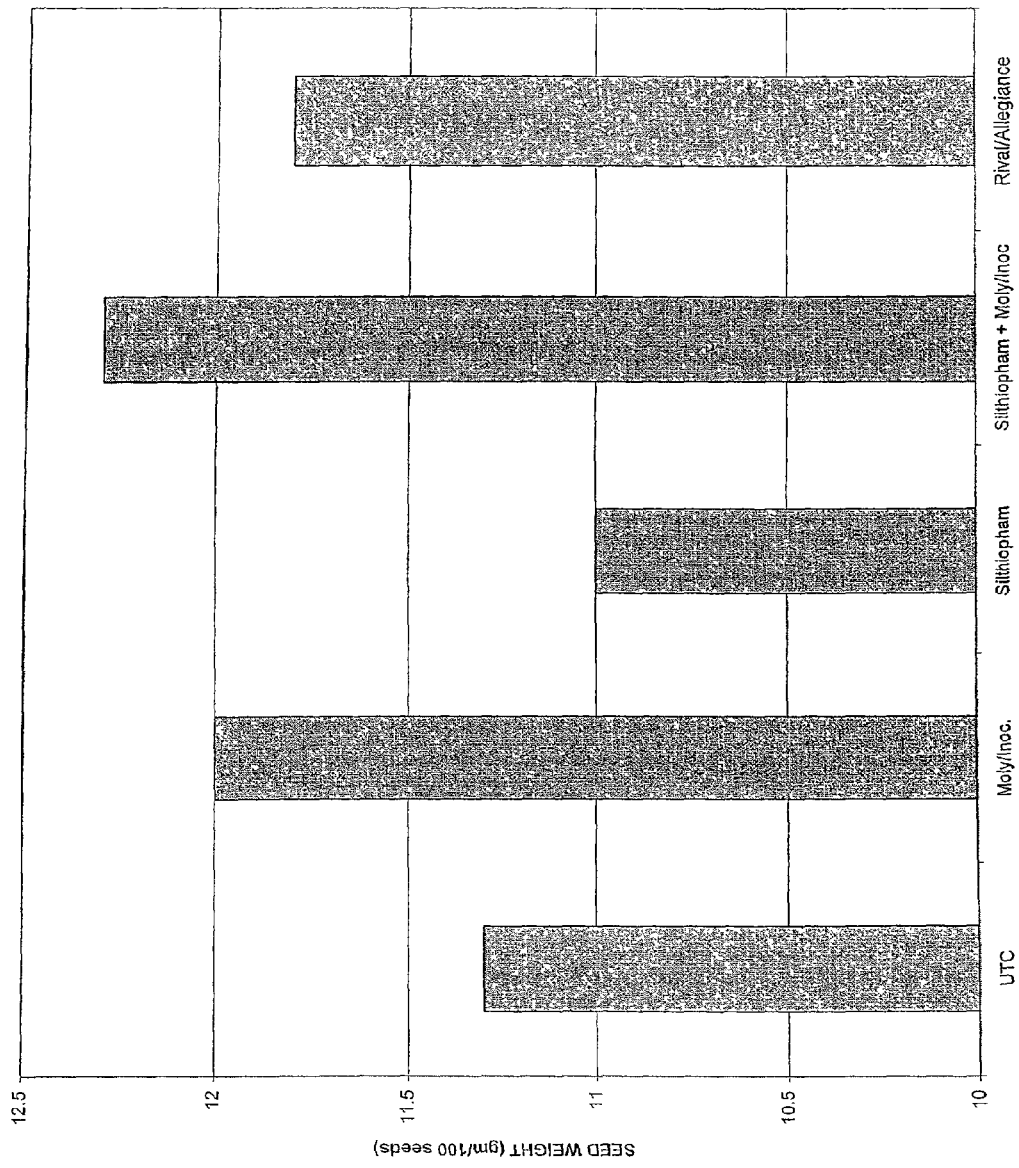
FIG. 4 shows the average seed weight of soybeans harvested in a field trial for soybeans receiving no treatment prior to (UTC) compared with soybeans that had been treated prior to planting with silthiopham (Silthiopham), silthiopham+inoculant (Silthiopham+Moly/Inoc), a sticker +inoculant (Moly/Inoc), and a standard fungicide treatment (Rival/Allegiance)
Figure 5:
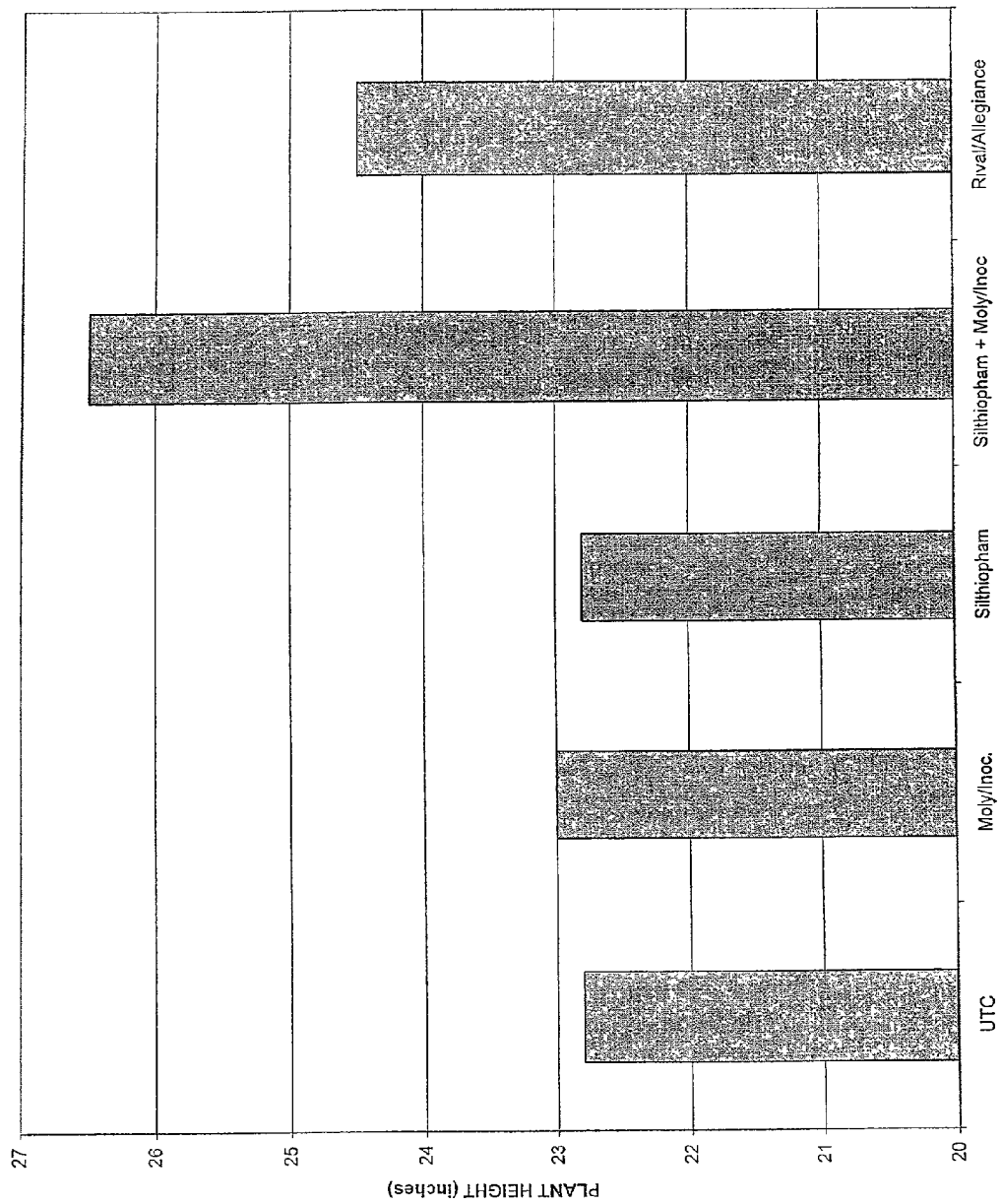
FIG. 5 shows the plant height of soybean plants in a field trial for soybeans receiving no treatment prior to (UTC) compared with soybeans that had been treated prior to planting with silthiopham (Silthiopham), silthiopham+inoculant (Silthiopham+Moly/Inoc), a sticker+inoculant (Moly/Inoc), and a standard fungicide treatment (Rival/Allegiance)

Notes
[a] Grain moisture for all treatments ranged 11.2% and 11.5%; plant lodging (1-5 scale with 1 being an erect plant and 5 being flat on the ground) for all treatments was 1.0; percent of plants showing Brown Stem Rot was 60% for all treatments; the test plot also reported severe incidence of feeding by bean leaf beetles.
[b] Grain yield was adjusted to 13% moisture for treatment Plant vigor was followed throughout the growing season, and FIG. 1 shows a plot of vigor as a function of time for the five different treatments. Likewise, FIG. 2 shows a plot of plant canopy as a function of time for the five treatments. In both cases, seeds treated with silthiopham+Mollyflo® and inoculant performed best, with seeds having only silthiopham treatment alone being similar to the untreated control. Seeds receiving either the Rival®/Allegiance® treatment or the The effect of treatment on seed weight and plant height is shown in FIGS. 4 and 5, respectively, and was similar to the effect on grain yield. Treatment with silthiopham+Mollyflo®+inoculant gave beans that were almost 9% larger, and plants that were about 16% taller than untreated control beans. In both cases, beans receiving only Mollyflo®+inoculant or Rival®/Allegiance® provided smaller increases, and beans receiving only silthiopham performed comparably with untreated beans.

The trial showed that beans grown from seed treated with silthiopham and a sticker/spreader formulation with an inoculant provided superior yields, superior bean weights, superior plant height and equaled the best vigor and canopy closure obtained by beans treated with only the inoculant, or only conventional fungicidal seed treatment with Rival®/Allegiance®.

EXAMPLE 3

This example shows the effect of the treatment of soybean seed with silthiofam on the yield and vigor of soybean plants in a field trial in South Africa.

Trials were conducted on five commercial soybean farms in different climatological areas in South Africa as shown in Table 3. Trial sites represent different soil types ranging from sandy to heavy clay. Trials included irrigation and dryland regions in the cool Highveld regions as the warmer Northern Transvaal.

TABLE 3

Soybean farms, soil types, irrigation status and soybeans cultivars used for the field trial.

| FARM NUMBER | DRYLAND or IRRIGATED | SOYBEAN CULTIVAR | SOIL TYPE |
|---|---|---|---|
| 1 | Irrigated | SNK500 | Loam |
| 2 | Irrigated | A5308 | Sandy loam |
| 3 | Dryland | Wenner90 | Clay loam |
| 4 | Dryland | SNK444 | Sand clay 12% |
| 5 | Dryland | SNK400 | Clay 40% |

Soybean seed for the trial was treated in the field and planted immediately thereafter. Seed that was to receive a treatment was initially covered with Mollyflo®, or a Mollyflo®+silthiopham mixture to insure uniform coating. When it was required, the peat-based inoculant was then added to the seed and thoroughly mixed to ensure an even coating. Rates of application of different seed treatments are shown in Table 4.

TABLE 4

Seed treatments.

| TREATMENT NUMBER | TREATMENT | SILTHIOPHAM | MOLLYFLO | INOCULANT |
|---|---|---|---|---|
| 1 | Untreated Control | 0 | 0 | 0 |
| 2 | Mollyflo + *Bradyrhizobium* inoculant | 0 | 400 ml/100 kg seed | 250 g/25 kg seed |
| 3 | Silthiopham + *Bradyrhizobium* inoculant | 200 ml Mollyflo + 200 ml silthiopham | 400 ml/100 kg seed | 250 g/25 kg seed |
| 4 | Silthiopham | 2 ml silthiopham/kg seed mixed in Mollyflo | 400 ml/100 kg seed | 0 |

Untreated soybeans and soybeans having the seed treatments shown in Table 4 were planted, cultivated and harvested according to local conventional practice. The following measurements were carried out on each farm:

Nodules: The number of nodules on plants in 400-mm rows was counted. Each set of plants was replicated seven times.

Plant weight: The plant weight (grams) of 2 meters per plot was measured in seven replications.

Seed yield: Seed yield was determined by harvesting 3-meter rows with seven replications. Plants were threshed with a plot-thresher and the seed was weighed with an electronic scale (±1 gram) and converted to kg/ha. An analysis of variance for yield on all 5 locations was conducted on the 95% reliability level.

Seed protein: Seed protein content was analyzed on 200 g samples of seed with an infrared protein analyzer.

Figure 6:
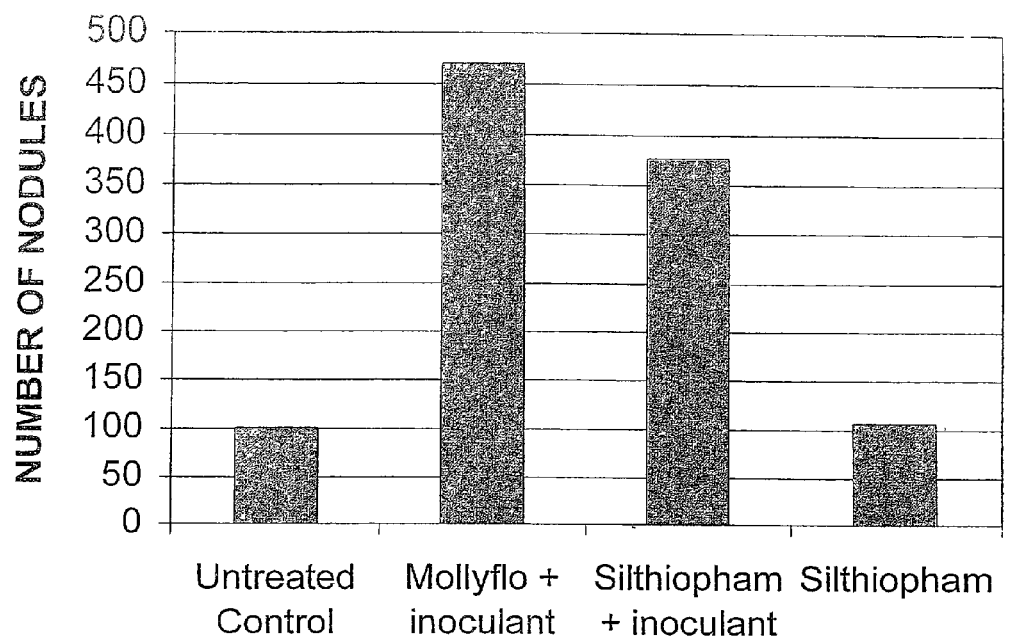
FIG. 6 shows the effect on the number of nodules on soybean plant roots for soybean plants at Farm #4 in a field trial of the treatment of soybean seeds prior to planting with a sticker+inoculant (Mollyflo+inoculant), silthiopham+inoculant (Silthiopham+inoculant) and Silthiopham alone, as compared with soybeans having no treatment (Untreated Control)
Figure 7:
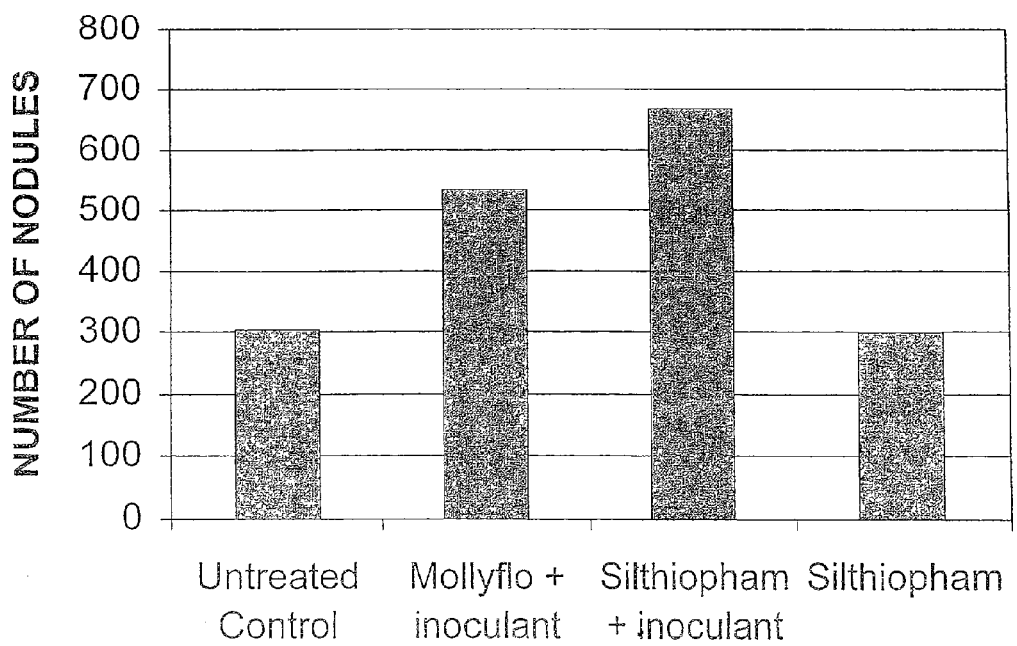
FIG. 7 shows the effect on the number of nodules on soybean plant roots at Farm #5 for soybean plants in a field trial of the treatment of soybean seeds prior to planting with a sticker+inoculant (Mollyflo+inoculant), silthiopham+inoculant (Silthiopham+inoculant) and Silthiopham alone, as compared with soybeans having no treatment (Untreated Control)

Results of the Trial:

Nodules: The number of nodules for the different seed treatments at farm numbers 4 and 5, respectively, is presented in FIGS. 6 and 7. The charts clearly show an increase in nodule numbers with the *Bradyrhizobium* inoculant treatments. The presence of silthiopham did not substantially affect the number of nodules compared with the standard Mollyflo®+inoculant treatment. Nodules visually appeared healthier where silthiopham was included in the treatment.

Figure 8:
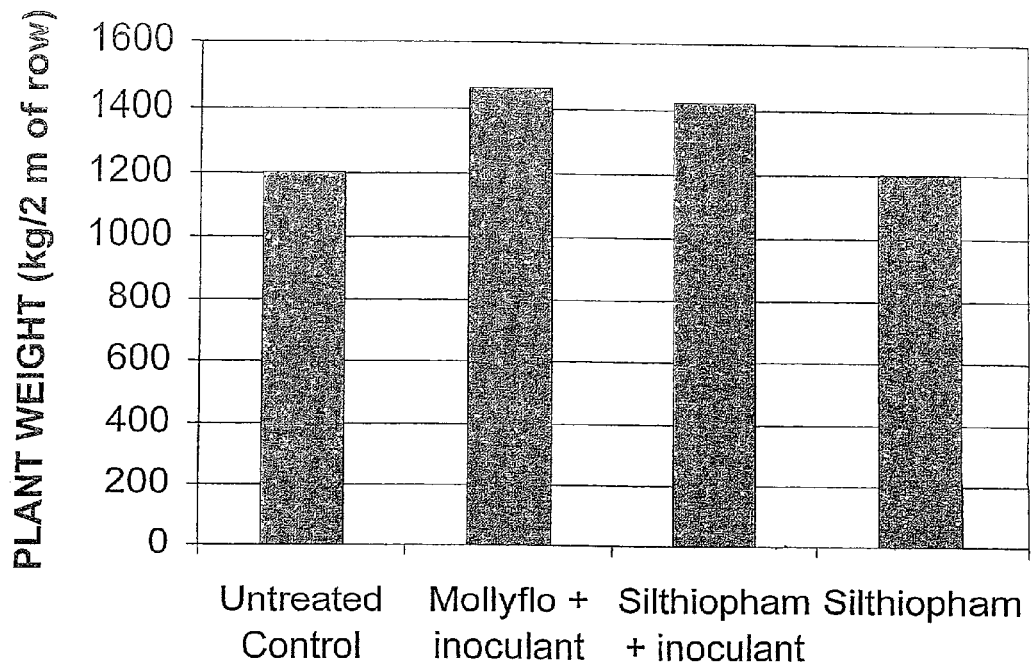
FIG. 8 shows the effect on plant weight for soybean plants at Farm #4 in a field trial of the treatment of soybean seeds prior to planting with a sticker+inoculant (Mollyflo+inoculant), silthiopham+inoculant (Silthiopham+inoculant) and Silthiopham alone, as compared with soybeans having no treatment (Untreated Control)
Figure 9:
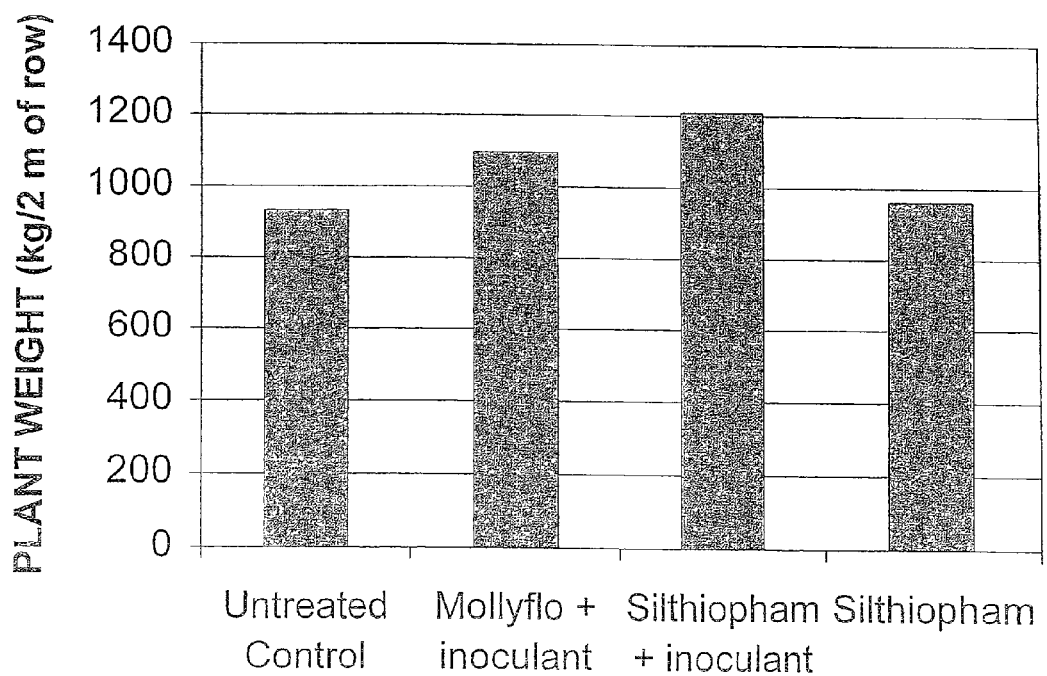
FIG. 9 shows the effect on plant weight for soybean plants at Farm #5 in a field trial of the treatment of soybean seeds prior to planting with a sticker+inoculant (Mollyflo+inoculant), silthiopham+inoculant (Silthiopham+inoculant) and Silthiopham alone, as compared with soybeans having no treatment (Untreated Control).

Plant weight: The weight of plants which grew from seeds having the different seed treatments is shown in FIGS. 8 and 9, respectively for farms 4 and 5. The charts indicate an increase in vegetative weight with the use *Bradyrhizobium* inoculant. The presence of silthiopham had no effect on plant weight compared to the standard Mollyflo®+inoculant treatment. The vegetative growth appeared visually greener and more vigorous for plants that had received silthiopham seed treatment compared to the standard treatment.

Seed Yield: The average seed yield for plants having the different seed treatments is shown in Table 5. Farms 1 and 2 were irrigated farms and farms 3-5 were dry land farms. Plants growing from seeds having the Mollyflo® and *Bradyrhizobium* inoculant treatment showed yield increases from 2144 kg/ha (no treatment) to 2583 kg/ha in dryland localities. Seed treatment with silthiopham+inoculant yielded 2783 kg/ha—an increase of almost 30% over the untreated control and almost 8% over the Mollyflo® and *Bradyrhizobium* inoculant treatment. For the two irrigated farms, seed treatment with silthiopham+inoculant provided a yield of 3011 kg/ha, compared with a yield of 2895 kg/ha from seeds having a standard treatment of Mollyflo® and *Bradyrhizobium* inoculant—an increase of about 4%.

In an analysis of the variance, the standard Mollyflo® and *Bradyrhizobium* inoculant treatment was compared with the silthiopham+inoculant treatment at all 5 localities. The use of silthiopham resulted in an average increase of 160 kg/ha (6.1%) for the five localities compared to the standard treatment. The analysis of variance showed a statistically significant difference between the two treatments at the 95% confidence level.

TABLE 5

Average soybean yield for different seed treatments on five farms.

| | | SOYBEAN YIELD (kg/ha)[a] | | |
|---|---|---|---|---|
| FARM | UNTREATED CONTROL | MOLLYFLO + INOCULANT | SILTHIOPHAM + INOCULANT | SILTHIOPHAM |
| 1 | n/a | 4049 | 4108 | n/a |
| 2 | n/a | 1741 | 1914 | n/a |
| Avg. | n/a | 2895 | 3011 | n/a |
| 3 | 2408 | 2100 | 2261 | n/a |
| 4 | 1838 | 2880 | 3151 | 1844 |
| 5 | 2187 | 2770 | 2937 | 2054 |
| Avg. | 2144 | 2583 | 2783 | 1949 |

Notes:
[a]n/a means that the data were not available.

The treatment of soybean seed with silthiopham in combination with *Bradyrhizobium* inoculants increased the grain yield of soybeans significantly compared to the standard Mollyflo®+*Bradyrhizobium* combination. Yields of beans treated with silthiopham alone did not significantly differ from the non-treated control. Visually, soybeans plants and nodules appeared healthier and greener for plants grown from seeds having silthiopham+inoculant treatment compared to seeds having the standard Mollyflo®+inoculant treatment.

EXAMPLE 4

This illustrates the activity of silthiopham on *Gaerumannomyces graminis* var. *tritici,* and on several microbial strains known to cause disease in soybeans.

In order to measure the activity of silthiopham on various microorganisms in in-vitro test method was used. The method was based on the measurement of the inhibition of mycelial growth on agar medium that included various levels of silthiopham. In the test method, three plugs from a growing plate of the desired pathogen culture are placed on Czapek-Dox agar plates that are amended with different concentrations of silthiopham. The concentrations tested were 0, 0.01, 0.1, 1.0, 10, and 100 µg/ml. Mycelium growth was measured on each plate after incubation for 4 days at 18° C. The $EC_{50}$ value was calculated for each test plate by fitting a log-log curve. A description of the method for determining the $EC_{50}$ value is provided by Nuninger-Ney et al., *In vitro test method for assessment of propiconazole sensitivity in Pyrenophora teres isolates*, FRAC Methods for Monitoring Fungicide Resistance, EPPO Bulletin, 21:291-354 (1991).

In the present test the fungicide medium preparation for the in vitro tests was a minimal medium (17.5 g Czapek Dox Broth, Co. Difco, 7.5 g Bacto-agar, Co. Difco, per 500 ml distilled or deionized water; pH=7.2; autoclaved for 20 min at 121°C.; 2.2 bar) amended with 50 µl of thiamine hydrochloride (c=1000 µg/ml, Co. Merck) and 50 µl of biotin dissolved in 5% ethanol (c=1000 µg/ml, Co. Merck). Both amendments, thiamine hydrochloride and biotin were added after sterilisation at a medium temperature of approximately 55° C.

A quantity of the active substance e.g. silthiofam was dissolved in methanol and added after sterilisation at 55° C. to the minimal medium to give the following concentrations in the agar medium: 0, 0.01, 0.1, 1, 10, and 100 µg/ml. Fungicide-amended medium is shaken vigorously and poured into sterile petri dishes (90×15 mm, ca. 25 ml medium per dish).

All tested fungi were growing on ¼ PDA (4.9 g Potato Dextrose Agar (Difco), 5.0 g Agar; 500 ml distilled water) at 18° C. for 6 days and than transferred on minimal medium (description see above). Mycelium plugs (6 mm) from the growing edge of an approximately two to six day old fungal culture were taken to conduct the in vitro fungicide test.

The baseline for *Gaerumannomyces graminis* var. *tritici* sensitivity was $EC_{50}$<6.7 µg/ml. The results for the test are shown in Table 6.

TABLE 6

Activity of silthiopham on *Gaeumannomyces graminis* var. *tritici* and microorganisms known to be pathogens of soybeans.

| PATHOGEN | DISEASE | ACTIVITY RATING (0-3)[a] | $EC_{50}$ (µg/ml)[b] |
|---|---|---|---|
| *Gaeumannomyces graminis* var. *tritici* | Take-all disease in cereals | 3 | 0.001 |
| *Fusarium solani,* var. *coeruleum* 4-2 | Root rot | 0 | 113.1 |
| *Fusarium solani,* var. *coeruleum* 4-5 | Root rot | 0 | 127.4 |
| *Fusarium solani,* var. *pisi* 34-1 | Root rot | 0 | 125.8 |
| *Fusarium solani,* var. *pisi* 34-2 | Root rot | 0 | 106.5 |
| *Rhizoctonia solani* 15-9 | Sheath blight | 0 | 162.4 |
| *Rhizoctonia solani* 15-10 | Sheath blight | 0 | 132.2 |
| *Fusarium oxysporum* var. *pisi* race1 33-9 | Root rot | 0 | 108.8 |
| *Fusarium oxysporum* var. *pisi* race1 33-10 | Root rot | 0 | 112.5 |
| *Fusarium oxysporum* var. *pisi* race1 33-11 | Root rot | 0 | 36,081 |
| *Septoria nodorum* | Glum blotch | 0 | n/a |
| *Phytopthera infestans* | Late blight | 0 | n/a |
| *Colletotrichum trifolii* | Root rot in alfalfa | 0 | n/a |

Notes:
[a]Activity rating: 0 = no, 1 = weak, 2 = good, 3 = excellent.
[b]"n/a" means that $EC_{50}$ values were not available or were not calculated.

The test results indicated that silthiopham had excellent activity against *Gaerumannomyces graminis* var. *tritici,* but had little or no activity against microorganisms that are known to be soybean pathogens. The results of these tests indicate that the yield increase or vigor increase is not due to better disease control by silthiopham but rather is unexpected.

EXAMPLE 5

This example illustrates a protocol for testing the effect on soybean yield and vigor of seed treatment prior to planting with silthiopham with and without an inoculant as compared with seeds having no treatment, seeds with only a sticking agent and an inoculant, and seeds that were treated with a commonly used pesticide combination with and without an inoculant and alone and in combination with silthiopham.

The following protocol provides a field trial that can be carried out to test the efficacy of soybean seed treatment with silthiopham as a function of several variables that are believed to be important for the present invention.

Soybean seeds of a selected variety are treated by the methods described in Example 3, except that the following treatments are used:

| TREATMENT NO. | DESCRIPTION |
|---|---|
| 1. | Untreated control |
| 2. | Seeds are treated with Mollyflo ® (4 ml/kg) and Inoculant (10 g/kg, applied at the time of planting). |
| 3. | Seeds are treated with Mollyflo ® (4 ml/kg), plus Rival ® (5 floz/cwt) and Allegiance ® (0.375 floz/cwt), plus Inoculant (10 g/kg, applied at the time of planting). |
| 4. | Seeds are treated with Mollyflo ® (4 ml/kg), plus 2 ml/kg of a Silthiopham formulation (having 125 g/l of active agent), plus Inoculant (10 g/kg, applied at the time of planting). |
| 5. | Seeds are treated with Rival ® (5 floz/cwt) and Allegiance ® (0.375 floz/cwt). |
| 6. | Seeds are treated with 2 ml/kg of a Silthiopham formulation (having 125 g/l of active agent). |
| 7. | Seeds are treated with Mollyflo ® (4 ml/kg), plus Rival ® (5 floz/cwt) and Allegiance ® (0.375 floz/cwt), plus 2 ml/kg of a Silthiopham formulation (having 125 g/l of active agent), plus Inoculant (10 g/kg, applied at the time of planting). |
| 8. | Seeds are treated with Mollyflo ® (4 ml/kg), plus Rival ® (5 floz/cwt) and Allegiance ® (0.375 floz/cwt), plus 4 ml/kg of a Silthiopham formulation (having 125 g/l of active agent), plus Inoculant (10 g/kg, applied at the time of planting). |

Stand count, vigor, time to maturity, plant height, seed yield and seed size are measured as described in Examples 2 or 3. The efficacy of silthiopham treatment of soybean seeds can then be determined as a function of the presence or absence or inoculant, and can be compared versus comparable treatments with other, commonly used, fungicides. It is believed that the results obtained from a trial using this protocol would reinforce the conclusions drawn from the results provided in Examples 2 and 3.

All references cited in this specification, including without limitation all papers, publications, patents, patent applications, presentations, texts, reports, manuscripts, brochures, books, internet postings, journal articles, periodicals, and the like, are hereby incorporated by reference. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description shall be interpreted as illustrative and not in a limiting sense.

What is claimed is:

1. A method of increasing the vigor and/or the yield of an agronomic plant selected from the genera *Vigna*, *Glycine*, *Vicia* and *Phaseolus*, wherein the method comprises treating the plant or its propagation material with a composition which comprises an effective amount of a fungicide having the formula

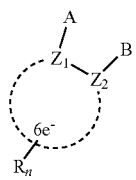

wherein $Z_1$ and $Z_2$ are C and are part of a thiophene ring;
A is selected from —C(X)-amine;
B is —$W_m$-$Q(R_2)_3$;
Q is C, or Si;
W is —$C(R_3)_p H_{(2-p)}$—
X is O;
n is 0, 1, or 2;
m is 0;
p is 0;
each R is independently selected from
a) halo, trimethylsilyl, and hydroxy;
b) $C_1$-$C_4$ alkyl, each optionally substituted with halo, or hydroxyl and
c) $C_1$-$C_4$ alkoxy, alkylthio, or alkylsulfinyl, each optionally substituted with halo;
each $R_2$ is independently selected from alkyl, each optionally substituted with halogen; and wherein, when Q is C, $R_2$ may also be selected from halo; and R3 is C1-C4 alkyl;
or an agronomic salt thereof, wherein the plant or its propagation material possesses a transgenic event providing the plant with resistance to glyphosate and the treatment comprises foliar application of glyphosate.

2. The method according to claim 1, wherein the fungicide is 4,5-dimethyl-N-2-propenyl-2-(trimethylsilyl)-3-thiophenecarboxamide.

3. The method according to claim 1, wherein treating the plant or propagation material comprises treating a seed of the plant with an inoculant selected from the group consisting of *Azospirillium* spp., *Rhizobium* spp., *Bradyrhizobium* spp., a mixture of *Rhizobium* spp. and *Bradyrhizobium* spp., and a mixture of either *Rhizobium* spp., or *Bradyrhizobium* spp. with any other microorganisms, and further includes foliar treatment of the plant with the fungicide, and foliar application of glyphosate.

4. The method according to claim 1, wherein treating the plant or its propagation material comprises applying the fungicide to the foliage of the plant in combination with glyphosate.

5. The method according to claim 4, wherein the fungicide is 4,5-dimethyl-N-2-propenyl-2-(trimethylsilyl)-3-thiophenecarboxamide.

6. The method according to claim 1, wherein treating the plant or its propagation material comprises treatment of a seed with an inoculant comprising *Azospirillium* spp., or *Rhizobium* spp., or *Bradyrhizobium* spp., or a mixture of *Rhizobium* spp. and *Bradyrhizobium* spp., or a mixture of either *Rhizobium* spp., or *Bradyrhizobium* spp. with any other microorganisms.

7. The method according to claim 1, wherein

A is —C(O)-amine, wherein the amine is substituted with a first and a second amine substituent or with an alkylaminocarbonyl and a hydrogen, —C(O)—SR$_3$, —NH—C(X)R$_4$, or —C(=NR$_3$)—XR$_7$ wherein R3 is C1-C4 alkyl; R4 is C1-C4 alkyl, haloalkyl, alkoxy, alkylthio, alkylamino, or dialkylamino; and R7 is C1-C4 alkyl, haloalkyl, or phenyl, optionally substituted with halo, nitro, or R$_4$;

the first amine substituent is selected from the group consisting of C$_1$-C$_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, C$_3$-C$_6$ cycloalkyl and C$_5$-C$_6$ cycloalkylkenyl; phenyl optionally substituted with one or more C$_1$-C$_4$ straight or branched alkyl, alkenyl, or alkynyl groups or mixtures thereof, cycloalkyl, cycloalkenyl, haloalkyl, alkoxy and nitro; C$_3$-C$_6$ cycloalkyl, C$_5$-C$_6$ cycloalkenyl, alkoxy, alkenoxy, alkynoxy, dialkylamino, and alkylthio;

and the second amine substituent is selected from the group consisting of hydrogen; C$_1$-C$_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl.

8. The method according to claim 7, wherein A is —C(O)-amine, wherein the amino radical is substituted with one or two groups selected from hydrogen; hydroxy; alkyl, alkenyl, and alkynyl, which may be straight or branched chain or cyclic; alkoxyalkyl; haloalkyl; hydroxyalkyl; alkylthio; alkylthioalkyl; alkylcarbonyl; alkoxycarbonyl; aminocarbonyl; alkylaminocarbonyl; cyanoalkyl; and mono- or dialkylamino.

9. The method according to claim 1, wherein Q is Si.

10. The method according to claim 9, wherein each R$_2$ is methyl.

11. The method according to claim 10, wherein A is alkylaminocarbonyl or dialkylaminocarbonyl.

12. The method according to claim 1, wherein the agronomic plant that is selected from the genera *Glycine*.

13. The method according to claim 1, wherein the agronomic plant is a soybean plant.

14. The method according to claim 1, wherein treating the plant or propagation material comprises treatment of a seed, wherein the seed is treated with an amount of the composition sufficient to include the fungicide in an amount that is within a range of about 0.1 gm/100 kg of seed to about 500 gm/100 kg of seed.

15. The method according to claim 14, wherein the seed is treated with an amount of the composition sufficient to include the fungicide in an amount that is within a range of about 10 gm/100 kg of seed to about 100 gm/100 kg of seed.

16. The method according to claim 14, wherein the seed is treated with an amount of the composition sufficient to include the fungicide in an amount that is within a range of about 20 gm/100 kg of seed to about 50 gm/100 kg of seed.

* * * * *

UNITED STATES PATENT AND TRADEMARK OFFICE
CERTIFICATE OF CORRECTION

PATENT NO. : 7,687,434 B2
APPLICATION NO. : 10/026301
DATED : March 30, 2010
INVENTOR(S) : Maurice R. De Billot It is certified that error appears in the above-identified patent and that said Letters Patent is hereby corrected as shown below:

Replace the term "Ceriotoma" with the term -- Cerotoma -- in Column 1, Line 52, of the issued Patent.

Replace the term "Gaerumannomyes" with the term -- Gaeumannomyces -- nineteen times throughout the issued Patent. The Column and line number for each time to replace the term "Gaerumannomyes" with the term -- Gaeumannomyces -- is as follows:

Column 2, Lines 6, 42, 44, 48 and 59; Column 7, Lines 39, 44 and 54; Column 8, Lines 12, 25, 29, 31, 37 and 47; Column 9, Line 1; Column 10, Line 23; Column 37, Line 35; Column 38, Lines 27 and 67.

Add the term "Q;" at the end of the sentence in Column 11, Line 20, of the issued Patent.

Replace the term "o-tolyi" with the term -- o-tolyl -- in Column 17, Line 31, of the issued Patent.

Replace the term "chioramben" with the term -- chloramben -- in Column 26, Line 59, of the issued Patent.

Replace the term "chioridazon" with the term -- chloridazon -- in Column 26, Line 59, of the issued Patent.

Replace the term "chiorimuron-ethyl" with the term -- chlorimuron-ethyl -- in Column 26, Line 60, of the issued Patent.

Replace the term "chiorotoluron" with the term -- chlorotoluron -- in Column 26, Line 60, of the issued Patent.

Replace the term "dichiobenil" with the term -- dichlobenil -- in Column 26, Line 66, of the issued Patent.

Replace the term "dichiorprop" with the term -- dichlorprop -- in Column 26, Line 66, of the issued Patent.

Signed and Sealed this

Nineteenth Day of October, 2010

David J. Kappos
*Director of the United States Patent and Trademark Office*

CERTIFICATE OF CORRECTION (continued)
U.S. Pat. No. 7,687,434 B2

Replace the term "giufosinate-ammonium" with the term -- glyfosinate-ammonium -- in Column 27, Line 12, of the issued Patent.

Replace the term "metolachior" with the term -- metolachlor -- in Column 27, Line 21, of the issued Patent.

Replace the term "dichioride" with the term -- dichloride -- in Column 27, Line 26, of the issued Patent.

Replace the term "thifensu lfuron-methyl" with the term -- thifensulfuron-methyl -- in Column 27, Line 40, of the issued Patent.

Replace the term "triflusu lfuron-methyl" with the term -- triflusulfuron-methyl -- in Column 27, Line 42, of the issued Patent.

Add the term "comparison." at the end of the last sentence below TABLE 2, in Column 33, Line 56, of the issued Patent.